US011744759B2

(12) United States Patent
Waterson et al.

(10) Patent No.: US 11,744,759 B2
(45) Date of Patent: Sep. 5, 2023

(54) METHOD AND APPARATUS FOR A MEDICAL CHAIR FOR REMOTE TESTING AND DIAGNOSIS

(71) Applicant: VideoKall, Inc., Bethesda, MD (US)

(72) Inventors: Vincent Anthony Waterson, Irvine, CA (US); David Sturgess, Chesterfield (GB)

(73) Assignee: VideoKall, Inc., Bethesda, MD (US)

( * ) Notice: Subject to any disclaimer, the term of this patent is extended or adjusted under 35 U.S.C. 154(b) by 323 days.

(21) Appl. No.: 16/882,030

(22) Filed: May 22, 2020

(65) Prior Publication Data

US 2020/0368090 A1    Nov. 26, 2020

Related U.S. Application Data

(60) Provisional application No. 62/851,909, filed on May 23, 2019.

(51) Int. Cl.
| | | |
|---|---|---|
| *A61G 15/10* | (2006.01) | |
| *A61G 15/02* | (2006.01) | |
| *A61B 7/04* | (2006.01) | |
| *A61B 5/00* | (2006.01) | |
| *G01G 19/44* | (2006.01) | |
| *A61B 5/022* | (2006.01) | |
| *A61B 5/091* | (2006.01) | |
| *G01B 17/00* | (2006.01) | |
| *G01G 19/52* | (2006.01) | |

(52) U.S. Cl.
CPC ............ *A61G 15/10* (2013.01); *A61B 5/0022* (2013.01); *A61B 5/022* (2013.01); *A61B 5/091* (2013.01); *A61B 5/70* (2013.01); *A61B 7/04* (2013.01); *A61G 15/02* (2013.01); *G01B 17/00* (2013.01); *G01G 19/44* (2013.01); *G01G 19/52* (2013.01)

(58) Field of Classification Search
CPC ...... A61G 15/10; A61G 15/02; A61B 5/0022; A61B 5/022; A61B 5/091; A61B 5/70; A61B 7/04; G01B 17/00; G01G 19/44; G01G 19/52
USPC ..................................................... 297/188.01
See application file for complete search history.

(56) References Cited

U.S. PATENT DOCUMENTS

| | | | |
|---|---|---|---|
| 3,222,105 | A | 12/1965 | Cross |
| 3,329,336 | A | 7/1967 | Ruys |
| 3,370,901 | A | 2/1968 | Andrews |
| 5,152,590 | A | 10/1992 | Dukes |

(Continued)

FOREIGN PATENT DOCUMENTS

| | | |
|---|---|---|
| GB | 1025327 A | 4/1966 |
| JP | 2018-051011 A | 4/2018 |

OTHER PUBLICATIONS

Search Report and Written Opinion issued in related application PCT/US2020/034355, dated Oct. 13, 2020, 17 pages.

*Primary Examiner* — Alex M Valvis
*Assistant Examiner* — Chanel J Jhin
(74) *Attorney, Agent, or Firm* — Leydig, Voit & Mayer, Ltd.

(57) ABSTRACT

A medical chair is provided for conducting and controlling in-depth medical exams from a remote location. Specifically, the medical chair allows for providing remote diagnoses and treatment, including a variety of testing procedures for patients with nonemergent but time sensitive illness or injury. The medical chair can be used in a semi-permanent, permanent, temporary, or mobile environment and includes stabilizing assemblies to adapt to any of these environments.

12 Claims, 34 Drawing Sheets

(56) References Cited

U.S. PATENT DOCUMENTS

| | | |
|---|---|---|
| 5,556,163 A | 9/1996 | Rogers, III et al. |
| 2008/0139893 A1 | 6/2008 | Lee et al. |
| 2009/0177128 A1 | 7/2009 | Fukuyama et al. |
| 2014/0265502 A1 | 9/2014 | Hough et al. |
| 2017/0202535 A1 | 7/2017 | Baudino |

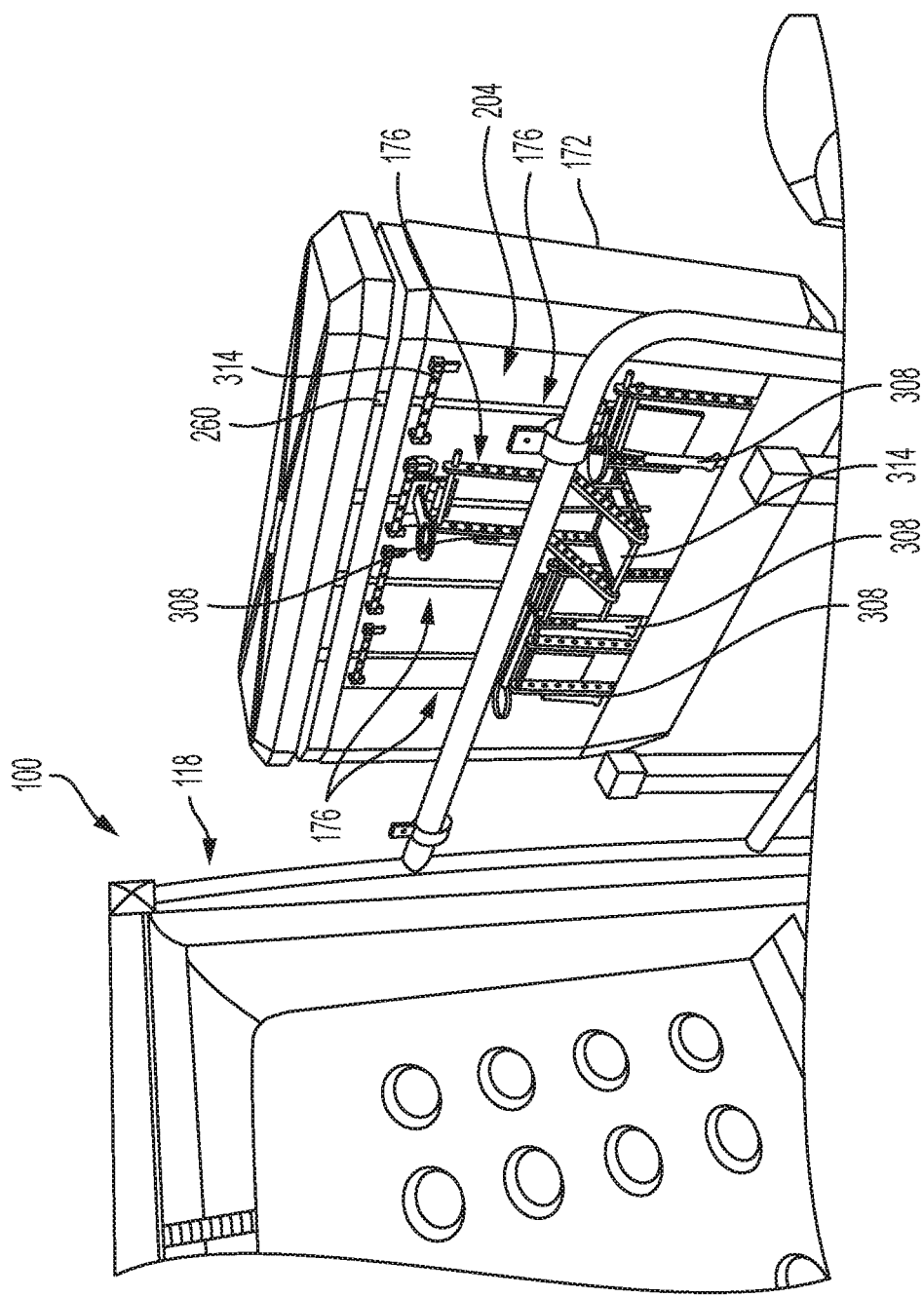

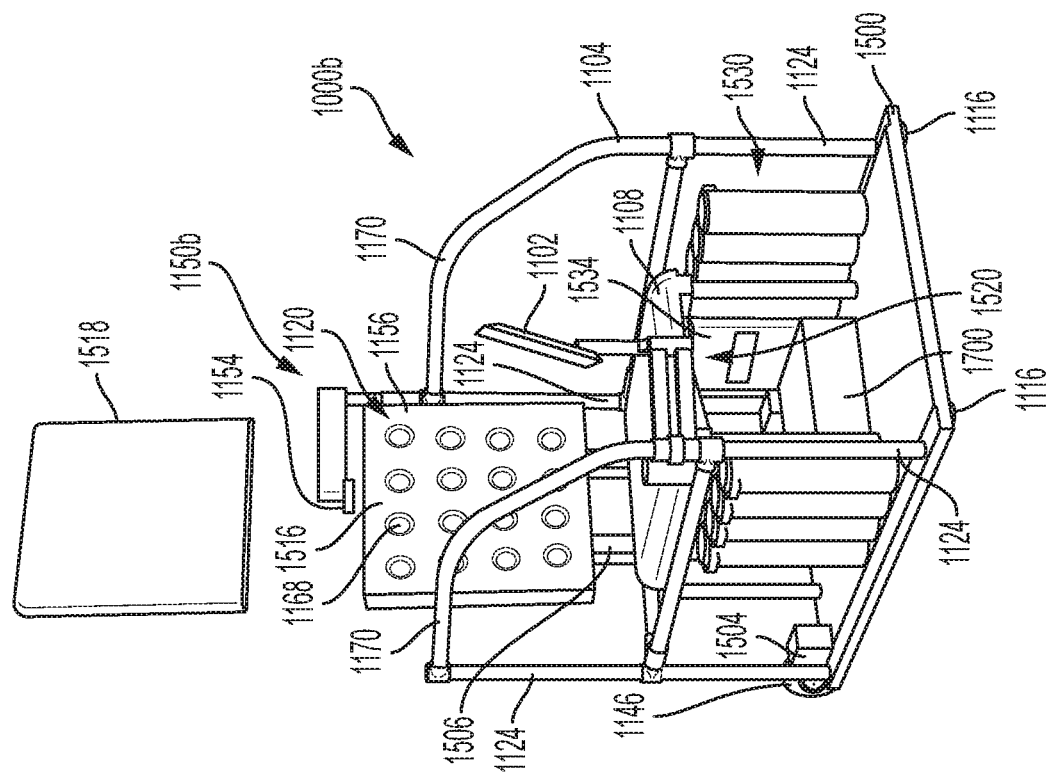
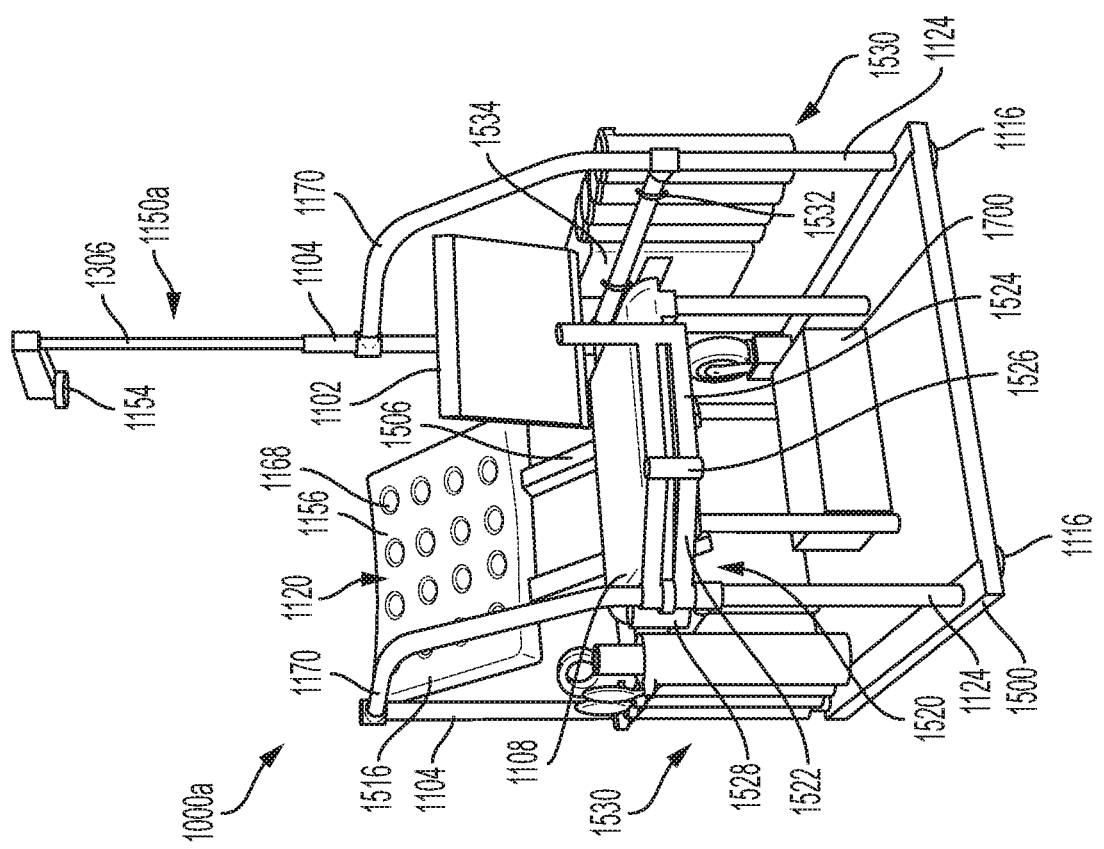
FIG. 29B
FIG. 29A

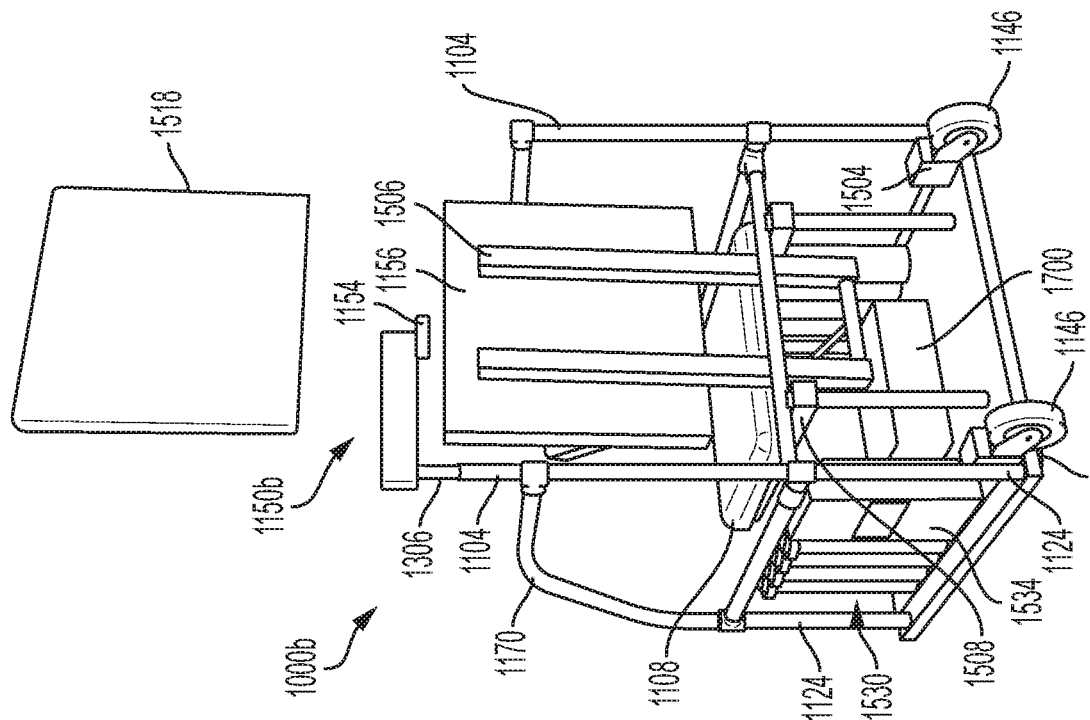
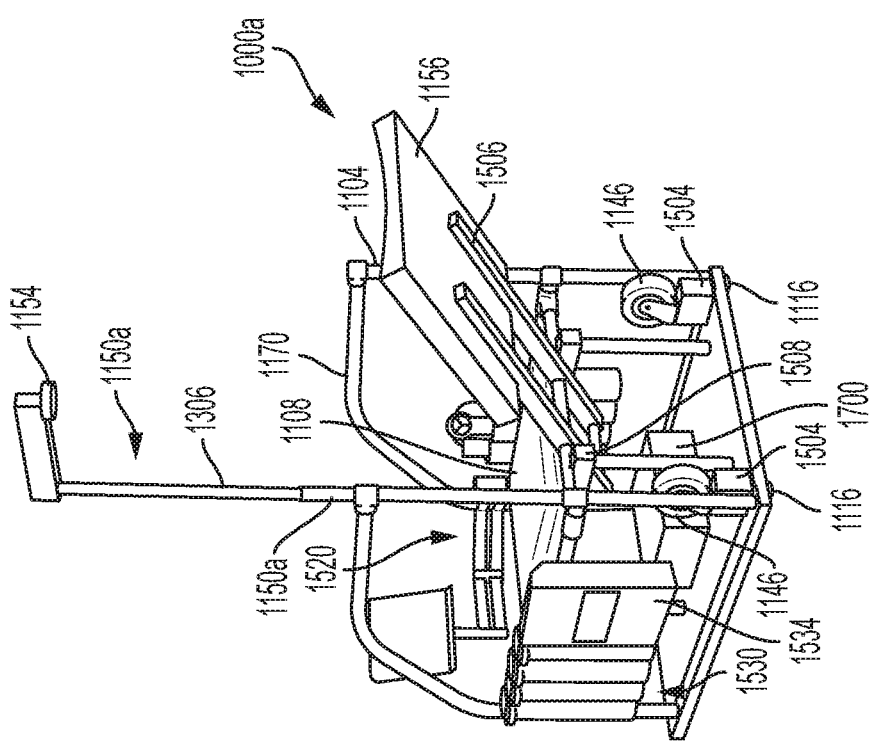
FIG. 30A
FIG. 30B

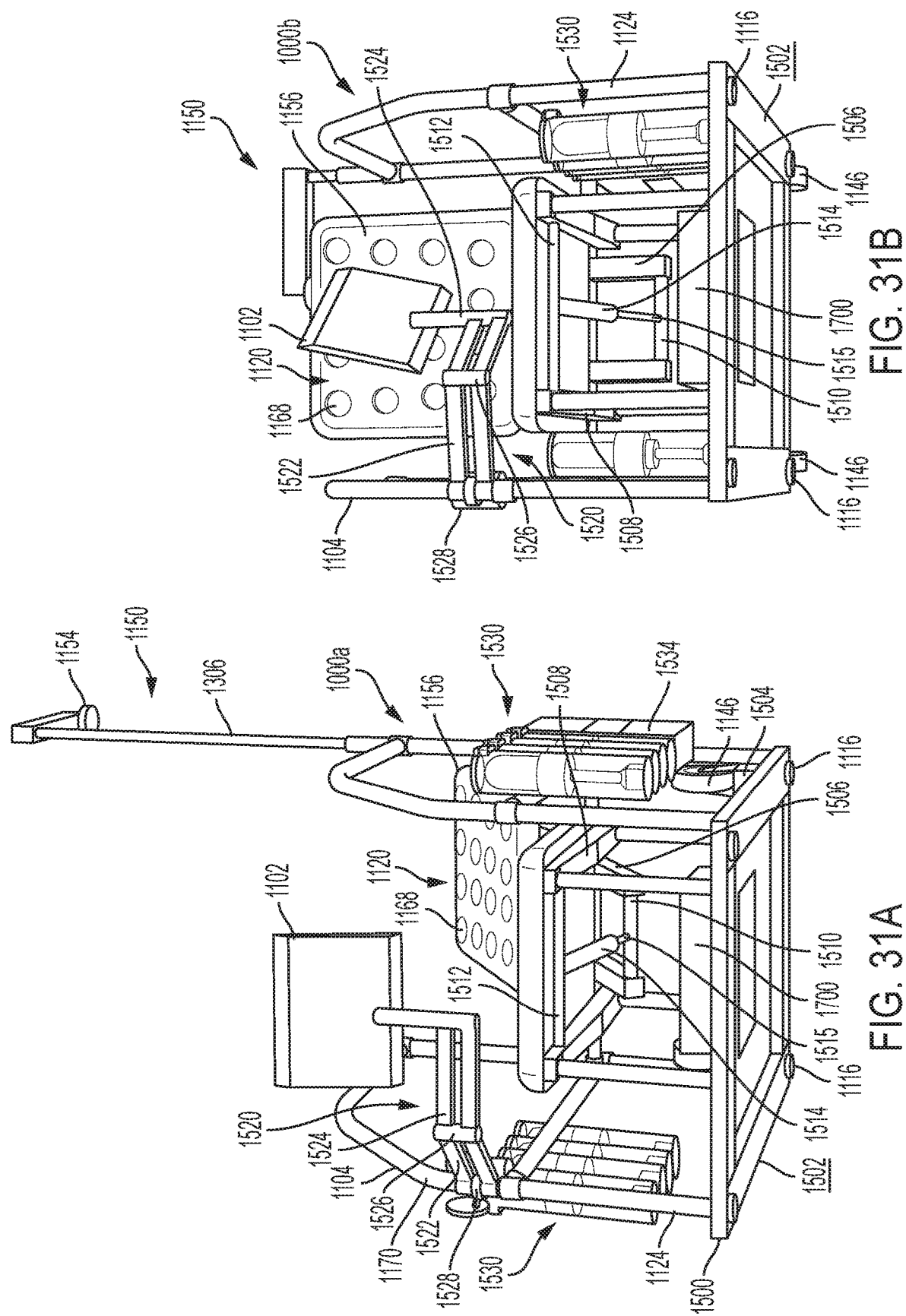

METHOD AND APPARATUS FOR A MEDICAL CHAIR FOR REMOTE TESTING AND DIAGNOSIS

CROSS-REFERENCE TO RELATED APPLICATIONS

The present application claims priority to U.S. Provisional Patent Application No. 62/851,909, filed May 23, 2019, the disclosure of which is hereby expressly incorporated by reference.

FIELD OF THE DISCLOSURE

The present disclosure relates to devices for facilitating treatment and diagnosis of patients. Specifically, the present disclosure relates to a medical chair for measuring vital signs and symptoms of a patient and transmitting such information to a local or remote medical practitioner for diagnosis and treatment of a condition of the patient in a quick and efficient manner.

BACKGROUND OF THE DISCLOSURE

Often patients who are unwell or injured are unable to be seen by a doctor in a time period allowing for a timely diagnosis and any subsequent treatment. Most of these patients are not in a serious condition warranting the high cost or increased traffic in a hospital emergency room or urgent care center. While some services provide instant or near-instant remote doctor consultations and diagnoses via teleconference or videoconference, such services rely on self-reporting of symptoms and vital signs, which may be unreliable and result in increased misdiagnoses and improper treatment. Quick, efficient service provided in a timely, reliable manner is needed for such patients.

SUMMARY OF THE DISCLOSURE

A medical chair is provided for conducting and controlling in-depth medical exams from a remote location. Specifically, the medical chair allows for providing remote diagnoses and treatment, including a variety of testing procedures for patients with nonemergent but time sensitive illness or injury. The medical chair can be used in a semi-permanent, permanent, temporary, or mobile environment and includes stabilizing assemblies to adapt to any of these environments.

In an embodiment of the disclosure, a medical chair assembly, comprising a frame, a seat coupled to the frame, and a back support coupled to the seat. The back support includes a stethoscope assembly comprising a plurality of sensors that are communicatively coupled to an acoustic control system, wherein the back support is configured for movement toward and away from the seat.

The back support may be curved. Each of the plurality of sensors may comprise a stethoscope sensor, and the sensors may be operably coupled to an acoustic amplifier. The medical chair assembly may further comprise an electronic data processing system, wherein each of the plurality of sensors are operably coupled to the electronic data processing system, and the electronic data processing system is coupled to a user interface remote from the medical chair assembly so that at least some of the plurality of sensors are controllable by the user interface.

The medical chair assembly may further comprise a longitudinal member that couples the back support to the seat, wherein the longitudinal member is threaded and engageable with a motor for rotational movement. The back support may move in a first direction when the longitudinal member rotates in a first direction, and the back support may move in a second direction when the longitudinal member rotates in a second direction. At least some of the plurality of sensors may be coupled to an actuator mechanism, the actuator mechanism configured to selectively deploy and retreat the coupled sensor relative to the back support. A membrane sleeve may be disposed on the back support to protect the plurality of sensors.

In another embodiment of the present disclosure, a medical chair assembly is disclosed, the medical chair assembly comprising a seat and a frame comprising a first handle on a first side of the seat; a docking station coupled to the first handle, the docking station housing an instrument assembly coupled to at least one instrument, wherein operation of the instrument assembly is configured to move the instrument assembly from a retracted configuration to a deployed configuration to position the instrument so that the instrument is at least partially exposed outside of the docking station.

The instrument assembly may comprise a motor, a threaded rod coupled to the motor and extending a direction away from the motor, and an instrument support operably coupled to the threaded rod so that when the threaded rod rotates in a first direction, the instrument support is configured to move along the threaded rod in a first direction and when the threaded rod rotates in a second direction, the instrument support is configured to move along the threaded rod in a second direction. Movement of the instrument support in the first direction may place the instrument assembly in the deployed configuration and movement of the instrument support in the second direction may place the instrument assembly in the retracted configuration.

At least one instrument may be tethered to the instrument assembly with a retractable cable. The instrument may be controllable using a user interface remote from the medical chair assembly. The docking station may comprise a lid or cover configured to prevent access to the instrument when the instrument assembly is in the retracted configuration. Direct contact between the instrument assembly and the lid or cover may open the lid or cover as the instrument assembly is moved from the retracted configuration to the deployed configuration.

The instrument assembly may be controllable using a user interface remote from the medical chair assembly. The frame may further comprise a second handle on a second side of the seat, wherein an additional instrument docking station may be coupled to the second handle. The instrument docking station may house a plurality of instrument assemblies. Each of the plurality of instrument assemblies may include a different instrument. A majority of the plurality of instrument assemblies may include a different instrument. The instrument docking station may be removably coupled to the first handle.

In yet another embodiment of the present disclosure, a deployment mechanism for a plurality of medical diagnostic sensors is disclosed, the deployment mechanism comprising a first frame plate; a spacer coupled to the first frame plate; a second frame plate coupled to the spacer opposite of the first frame plate; a motor coupled to either of the first frame plate or the second frame plate, the motor operatively coupled to a gear and a microcontroller configured to control the motor; a key selectively received between the first frame plate and the second frame plate, the key defining an internal rack configured to cooperate with the gear and including a mount; and a sensor coupled to the mount.

The deployment mechanism may further comprise a signal receiver coupled to the first frame plate and communicatively coupled to the microcontroller, and a signal transmitter coupled to the second frame plate so that the signal receiver and the signal transmitter are in selective communication, wherein the key may define at least one aperture to place the signal receiver and the signal emitter in selective communication. The microcontroller may be configured to place the motor in operation if the signal receiver unexpectedly loses contact with the signal emitter. Rotation of the gear in a first direction may move the key in a first direction so that the mount moves away from the first frame plate and the second frame plate, while rotation of the gear in a second direction may move the key in a second direction so that the mount moves toward the first frame plate and the second frame plate.

In yet another embodiment of the present disclosure, a medical diagnostic instrument docking station is disclosed, the docking station comprising: a base, a motor coupled to the base; a threaded rod coupled to the motor and extending in a direction away from the motor; a first tube coupled to the base so that the motor and the threaded rod are contained within the first tube; a flappable lid rotatably coupled to the first tube opposite form the base; and a second tube disposed within the first tube, the second tube coupled to a disc operatively coupled to the threaded rod, the second tube defining a chamber configured to receive an instrument, the second tube further defining an extension extending from the second tube in a direction opposite of the disc, the extension configured to selectively contact the flappable lid.

Rotation of the threaded rod in a first direction may raise the second tube along the threaded rod in a direction toward the flappable lid and rotation of the threaded rod in a second direction may lower the second tube along the threaded rod in a direction away from the flappable lid. The extension may contact the flappable lid to open the flappable lid as the second tube is raised. The second tube may house an instrument. The instrument may be tethered to the second tube by a cable. The second tube may be coupled to a retraction spool, wherein the instrument may be tethered to the retraction spool by a cable. The instrument docking station may further comprise a sensor coupled to the second tube, the sensor configured to register the presence of the instrument within the second tube.

In another embodiment of the present disclosure, a method of deploying and retracting an array of stethoscopic sensors for monitoring vital signs of a person, the method comprising: operating a motor, the motor operably coupled to a gear configured to rotate upon operation of the motor; engaging the gear with a rack defined by a key so that the key moves in a first direction, the key further defining at least one slot, wherein the key is movably disposed between a first frame plate and a second frame plate; placing a signal emitter coupled to the first frame plate in communication with a signal receiver coupled to the second frame plate, wherein the signal emitter and the signal receiver are placed in communication through the at least one slot of the key and the signal receiver is communicatively coupled to the microcontroller; and exposing a sensor coupled to the key.

The method may further comprise engaging the gear with the rack so that the key moves in a second direction and retracting the sensor. When the signal emitter and the signal receiver unexpectedly lose communication, the microcontroller may be configured to automatically operate the motor until the signal emitter and the signal receiver are placed in communication. The sensor may be selectively communicatively coupled to an audio system of a computer. The sensor may not be communicatively coupled to the audio system when the key is in motion. The key may define a first slot and a second slot, each of the first slot and the second slot facilitating communication of the signal emitter and the signal receiver. The signal emitter and the signal receiver may be placed in communication through the first slot when the sensor is exposed, and the signal emitter and the signal receiver may be placed in communication through the second slot when the sensor is unexposed.

In yet another embodiment of the present disclosure, a method of deploying a plurality of medical diagnostic instruments from an instrument docking station is disclosed, the method comprising operating a motor, the motor operably coupled to a threaded rod so that the threaded rod rotates in a first direction with operation of the motor, the threaded rod and the motor contained by a first tube; raising a second tube coupled to the threaded rod by a disc, the second tube disposed within the first tube and containing an instrument; contacting a lid of the first tube with an extension defined by the second tube; opening the lid of the first tube by exerting force on the lid with the extension; and exposing at least a portion of the instrument on the outside of the first tube.

A user may remove the instrument from the second tube to operate the instrument. The instrument may be tethered to the second tube by a cable. The method may further comprise placing the instrument in the second tube and sensing the presence of the instrument in the second tube with a sensor disposed on or near a bottom surface of the second tube. The method may further comprise operating the motor so that the threaded rod rotates in a second direction; lowering the second tube; removing contact of the lid by the extension; and closing the lid.

In another embodiment of the present disclosure, a method of treating a patient is disclosed, the method comprising interacting with a first user interface to place the first user interface in communication with a second user interface, the first user interface and the second user interface operable to exchange data when the first user interface and the second user interface are remote from each other, the first user interface coupled to a medical chair, and completing at least one of the following: measuring a blood pressure of a patient with a blood pressure cuff, the blood pressure cuff coupled to a frame of the medical chair and placed into operation using the second user interface; deploying an instrument from an instrument docking station coupled to the frame of the medical chair, the instrument docking station placed into operation using the second user interface; measuring a height of the patient with a height sensor coupled to the frame of the medical chair, the height sensor placed into operation using the second user interface; measuring a respiratory or vascular vital sign of the patient with a stethoscope array of a back support, the stethoscope array placed into operation using the second user interface; measuring a respiratory vital sign of the patient with a spirometer, the spirometer coupled to the frame of the medical chair, the spirometer placed into operation using the second user interface; and measuring a weight of the patient with a plurality of weight sensors coupled to the medical chair, the weight sensors placed into operation using the second user interface.

The medical chair may be mounted on an auto-level device, the auto-level device comprising a first frame for elevating the medical chair from a surface beneath the medical chair and a second frame for mounting of the medical chair, the second frame coupled to a first leveling motor configured to tilt the second frame about a first axis. A positioning module may be coupled to the second frame, the positioning module operably coupled to an accelerometer operably coupled to a central computer of the medical chair, wherein the accelerometer may be configured to determine whether the medical chair is on a level surface.

The method may further comprise determining whether the medical chair is positioned on a level surface, wherein when the medical chair is not positioned on a level surface, operating the first leveling motor to tilt the second frame, and, wherein when the medical chair is positioned on a level surface or the second frame has placed the medical chair on a level surface, ceasing operation of the first leveling motor. The auto-level device may further comprise a third frame coupled to the second frame, the third frame coupled to a second leveling motor configured to tilt the third frame about a second axis. The first axis may be generally transverse to the second axis. The medical chair may be positioned in a semi-permanent or permanent environment. The medical chair may be mounted within a vehicle.

Additional features and advantages of the present disclosure will become apparent to those skilled in the art upon consideration of the following detailed description of the illustrative embodiments exemplifying the disclosure as presently perceived.

BRIEF DESCRIPTION OF THE DRAWINGS

The detailed description of the drawings particularly refers to the accompanying figures in which:

FIG. 14 is a perspective cross-sectional view of an instrument docking station of the medical chair of FIG. 1;

FIG. 29A is a perspective view of a second exemplary embodiment of a medical chair configured to communicatively couple with a medical practitioner interface to receive testing, diagnosis, and/or treatment from a medical practitioner remote from the medical chair, the medical chair in a deployed configuration;

FIG. 29B is a perspective view of the medical chair of FIG. 29B in an undeployed configuration;

FIG. 30A is a rear perspective view of the medical chair of FIG. 29A;

FIG. 30B is a rear perspective view of the medical chair of FIG. 29B;

FIG. 31A is a bottom-up perspective view of the medical chair of FIG. 29A;

FIG. 31B is a bottom-up perspective view of the medical chair of FIG. 29B;

DETAILED DESCRIPTION OF THE DRAWINGS

Figure 1:
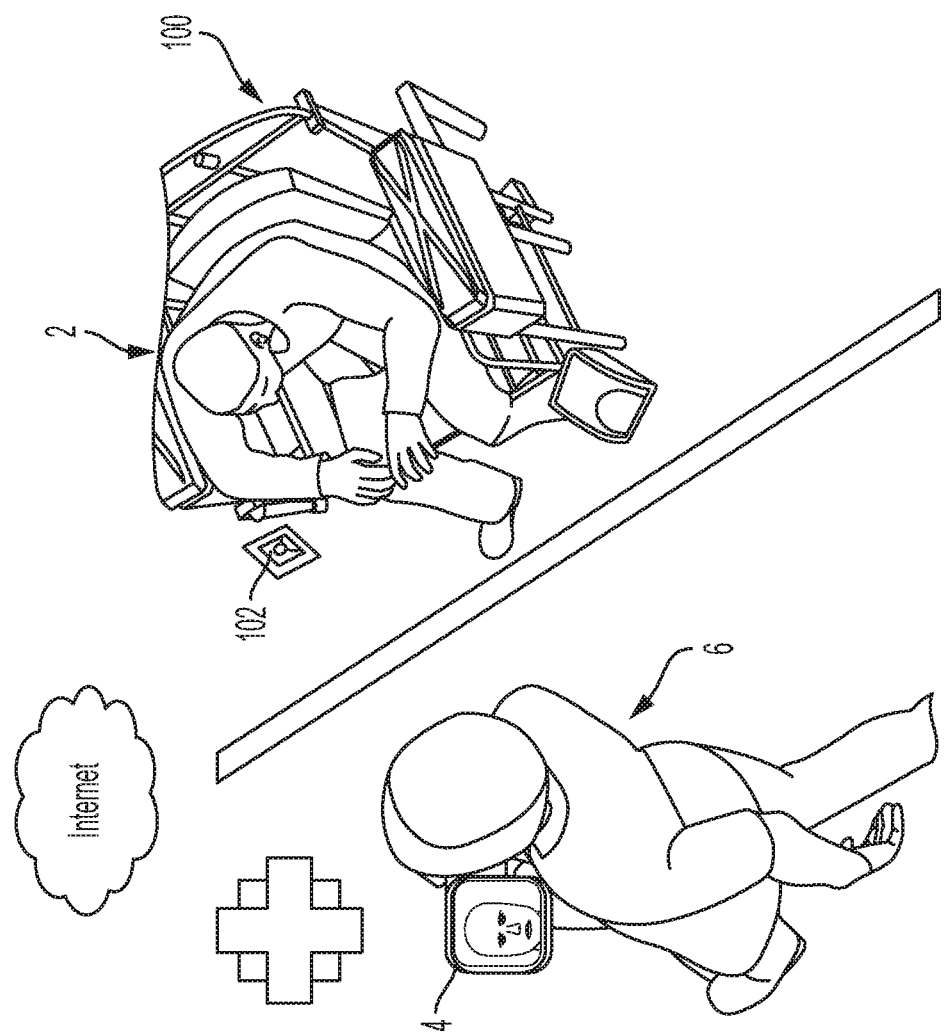
FIG. 1 illustrates a remote testing and diagnosis arrangement, wherein a patient utilizes a medical chair communicatively coupled with a medical practitioner user interface, such as a supervisory terminal, to receive testing, diagnosis, and/or treatment from a medical practitioner remote from the medical chair.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates an embodiment of the invention, and such an exemplification is not to be construed as limiting the scope of the invention in any manner. Furthermore, certain features and components as described herein may be added schematically to merely indicate the positioning and existence of such features and components. Such schematic features include at least a variety of magnets, sensors, pins, springs, apertures, pillow blocks, cables, electronic components, and others.

Referring to FIG. 1, a medical chair 100 is illustrated in use by a patient 2. The medical chair 100 illustratively includes a patient user interface 102 that is in communicative contact with a medical practitioner user interface 4 of a physician, nurse practitioner, or other medical practitioner 6. Illustratively, the patient user interface 102 and the medical practitioner user interface 4 are connected to the Internet by wireless signal, allowing the communication between the medical practitioner user interface 4 and the patient user interface 102 to occur from relatively remote locations. In other embodiments, the medical practitioner user interface 4 and the patient user interface 102 may be connected by Bluetooth®, wires, or other communicative coupling methods as known by one of ordinary skill in the art.

As described further herein, the patient 2 may utilize the patient user interface 102 and different functions and accessories of the medical chair 100 discussed further herein to communicate to the medical practitioner 6. Such communication allows for the medical practitioner 6 to review the symptoms and vital signs of the patient to provide a diagnosis to the patient in real-time, further allowing treatment of the patient's condition in a timely and efficient manner, whether the medical practitioner 6 and the patient 2 are in separate locations relatively remote from the other or in relatively close contact.

Figure 2:
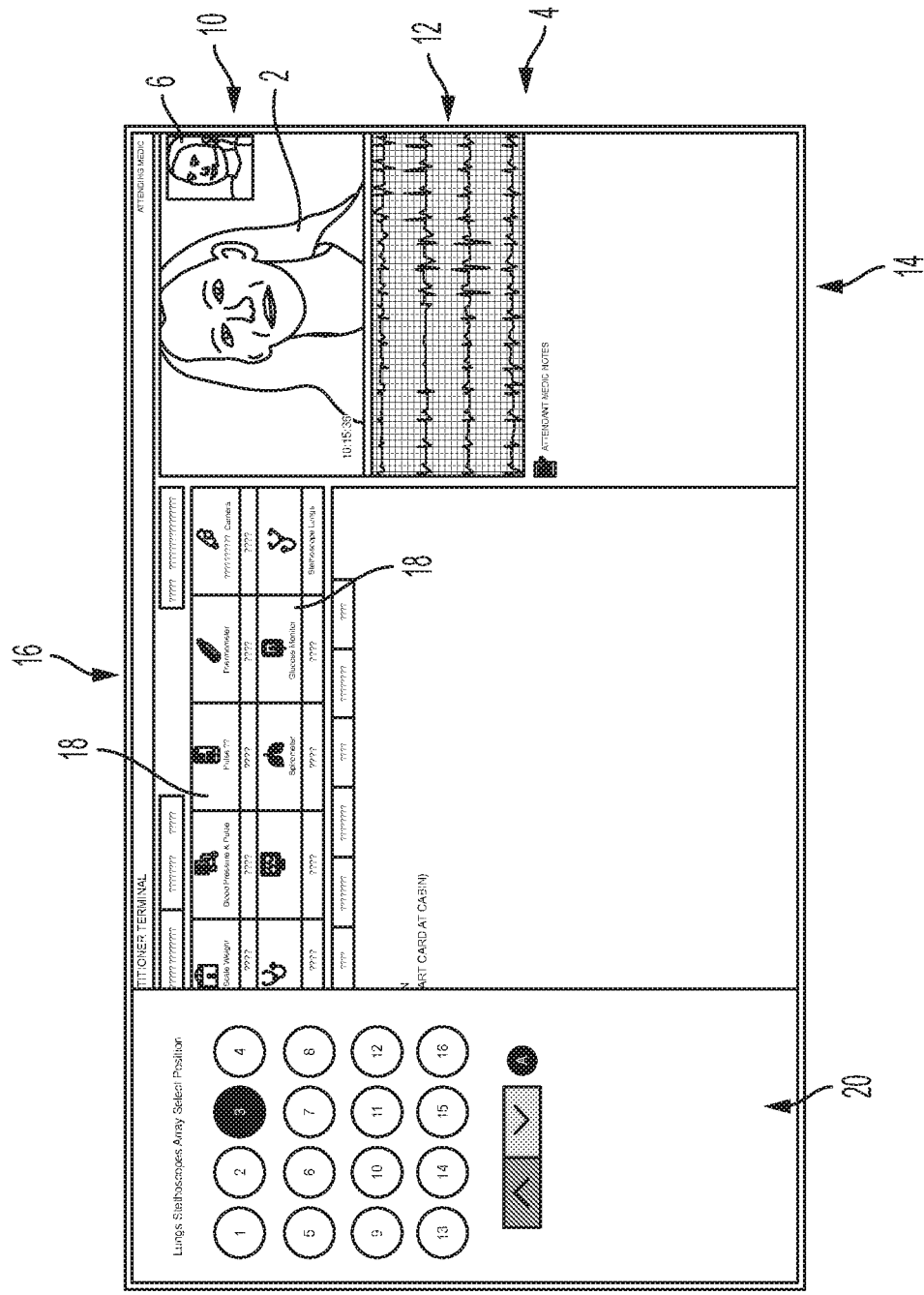
FIG. 2 is an exemplary illustration of the medical practitioner user interface, or supervisory terminal, of FIG. 1.

An exemplary medical practitioner user interface 4 is illustrated by FIG. 2. The medical practitioner user interface 4 may have a varying appearance but is generally configured to accomplish the functions as described herein. The medical practitioner user interface 4 may comprise any of a variety of hardware, including permanent or semi-permanent supervisory terminal, a mobile computer such as a tablet, smart phone, or laptop, or a variety of other computer hardware configurations having a graphic user interface. The medical practitioner user interface 4 may include a video chat window 10 to allow virtual face-to-face visual and auditory communication between the patient 2 and the medical practitioner 6. A monitoring window 12 may be included to allow the medical practitioner 6 real-time monitoring of a patient's vital signs as needed. A notepad 14 may also be available so that the medical practitioner 6 can take and keep notes for each patient, and, illustratively, for each metric.

The medical practitioner user interface 4 includes a control menu 16 that allows the medical practitioner 6 to remotely control functions of the medical chair 100 (FIG. 1). The control menu 16 may include a plurality of graphics 18, each graphic 18 corresponding to a particular component or function of the medical chair 100 (FIG. 1) as further described herein. In other embodiments, the control menu 16 may include a list of components that can be remotely controlled by the medical practitioner 6 using the medical practitioner user interface 4. After selecting a component form the control menu 16, a submenu 20 may appear on the medical practitioner user interface 4 as needed.

Figure 3:
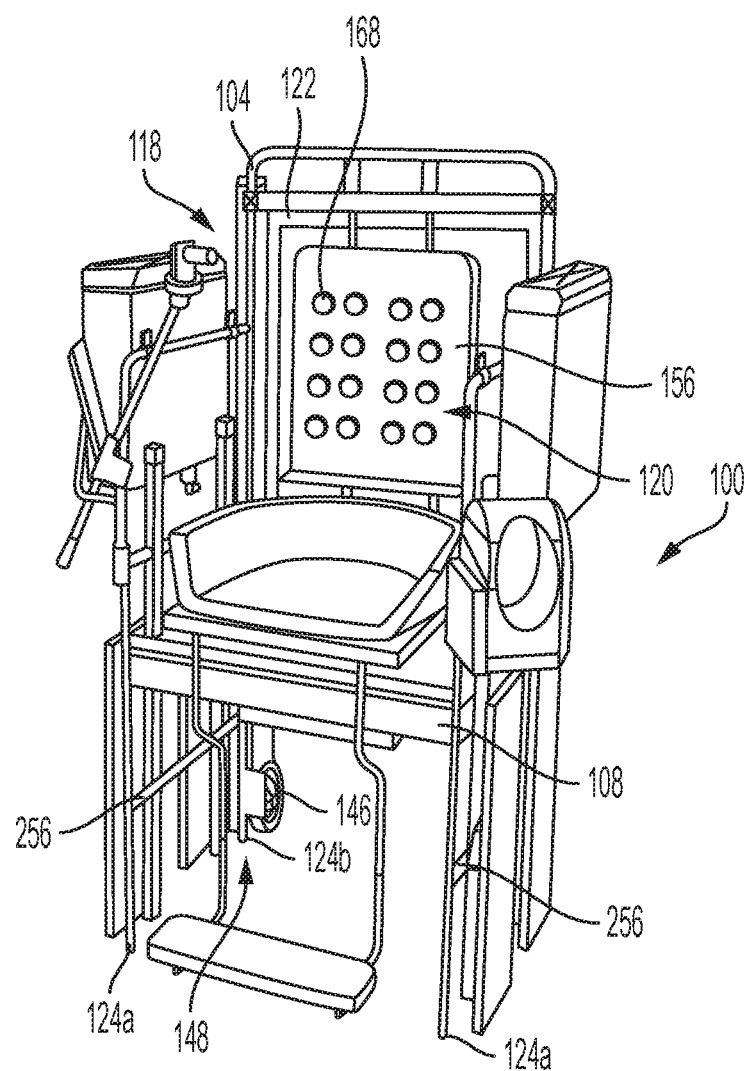
FIG. 3 is a perspective view of the medical chair of FIG. 1, the medical chair in an undeployed configuration.

Now referring to FIG. 3, an embodiment of the medical chair 100 is shown. The medical chair 100 includes a tube frame 104 to provide the general overall structure of the medical chair 100. The tube frame 104 defines a plurality of legs 124 to provide initial support to the medical chair 100, including a pair of front legs 124a and a corresponding pair of rear legs 124b. Each of the front legs 124a may couple to its corresponding rear leg 124b additionally via a crossbar 256 to provide extra stability to the medical chair 100.

Illustratively, the tube frame 104 is comprised of a plurality of hollow tubes configured to receive power and data cables to supply data and power between electrical components and information systems of the medical chair 100 as described further herein. The hollow tubes comprising the tube frame 104 may include a variety of tubes, including straight tubes, 90° curve tubes, 145° curve tubes, and T-shaped tubular sections. The hollow tubes may include a circular cross-section as shown, and in other embodiments may have a rectangular, triangular, or other cross-section shape. In some embodiments, the cables may be routed through the plurality of hollow tubes and then coupled together to form the tube frame 104 via adhesive, welding, mechanical fasteners, or other coupling mechanisms as known in the art. In other embodiments, the tube frame 104 may be formed using a continuous hollow tube formed in the desired shape of the tube frame 104 before or after the routing of the cables. The tube frame 104 may be comprised of a lightweight metal, such as aluminum. In other embodiments, the tube frame 104 may be comprised of other metals, metal alloys, or various polymers.

Figure 4:
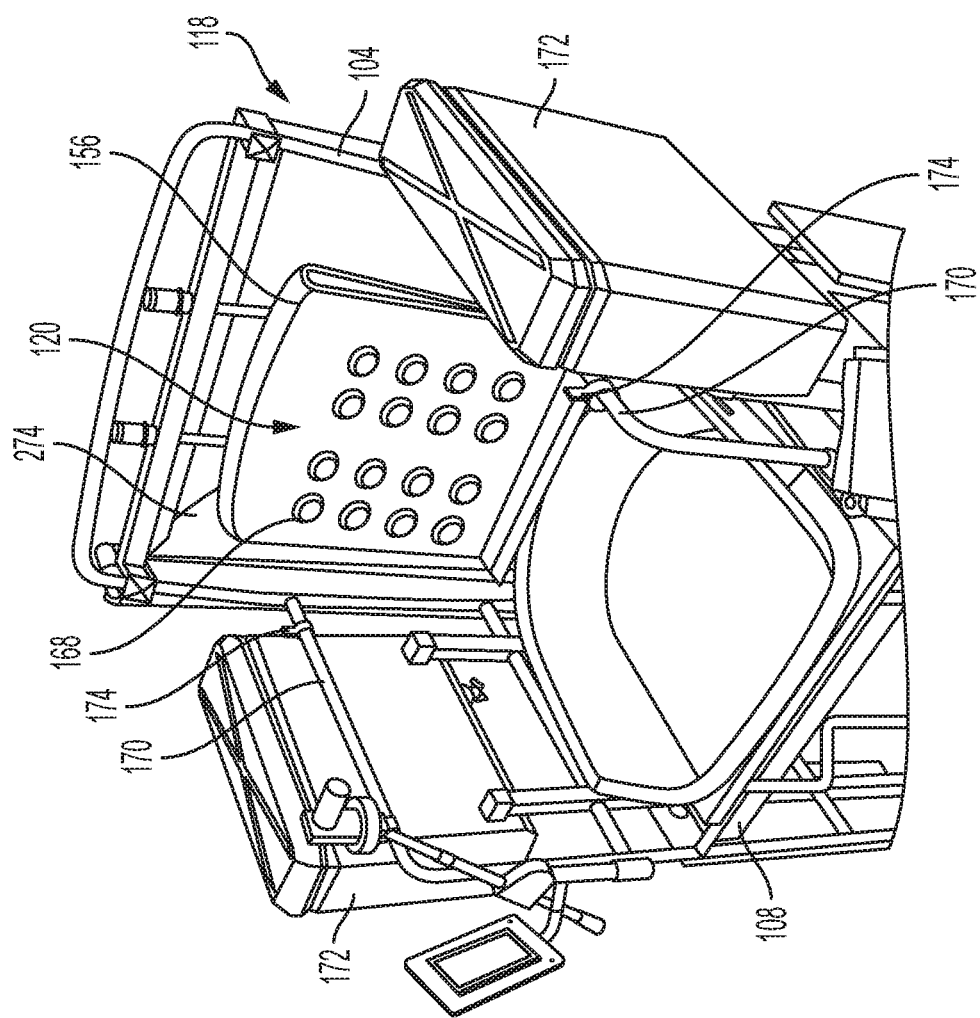
FIG. 4 is a perspective view of the medical chair of FIG. 3, including an illustration of a seat back of the medical chair.

Referring additionally to FIG. 4, the tube frame 104 supports a seat 108 and a chair back 118. The chair back 118 includes an electronics enclosure 122 supported by the tube frame 104 and a back support 156 coupled to the seat 108 and operatively coupled to the electronics enclosure 122 as described further herein. A front side 274 of the electronics enclosure 122 located closest to the back support 156 may at least partially form a concave shape for receiving the back support 156 to provide an efficient use of space. The back support 156 includes a stethoscope array 120 configured to contact a patient's back when the patient is seated in the medical chair 100. The stethoscope array 120 is comprised of a plurality of electric sensors 168, such as piezo electric sensors, disposed on the back support 156 in a shape ideally mimicking the shape of a human lung. In other embodiments, the electric sensors 168 may be positioned on the back support 156 in any shape that facilitates the measurement of respiratory and/or vascular vital signs. Additionally, the back support 156 may be curved to provide a more ergonomic shape and further compliment the shape of the patient's torso to better facilitate proper positioning of the electric sensors 168 relative to the patient.

Each of the electric sensors 168 are operatively coupled to a channel analog multiplexer 242 (FIG. 23) operatively coupled to an acoustic amplifier, or audio amplifier 244 (FIG. 23), each of the channel analog multiplexer 242 and the audio amplifier 244 contained in the electronics enclosure 122. The audio amplifier 244 (FIG. 23) is communicatively coupled with an electronic data processing system, or central computer 238 (FIG. 23), described further herein, the central computer 238 including an acoustic control system. The electronics enclosure 122 allows for convenient storage of conventional electronics, including a microcontroller 246 (FIG. 23), for movement of the back support 156 as described further herein. Other conventional electronics for operation of the medical chair 100 may further be stored within the electronics enclosure 122.

Figure 5:
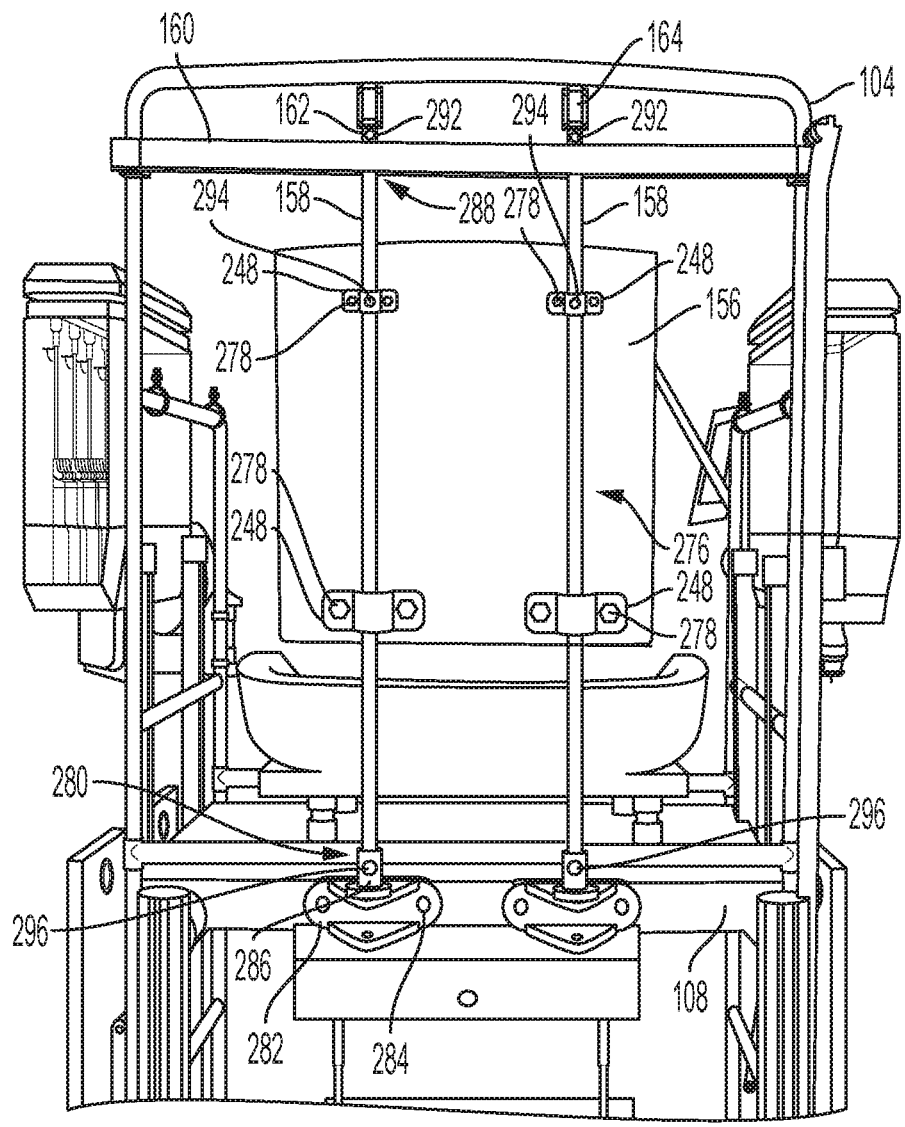
FIG. 5 is a rear cross-sectional view of the medical chair of FIG. 4, wherein a portion of the seat back of FIG. 4 has been removed.
Figure 6:
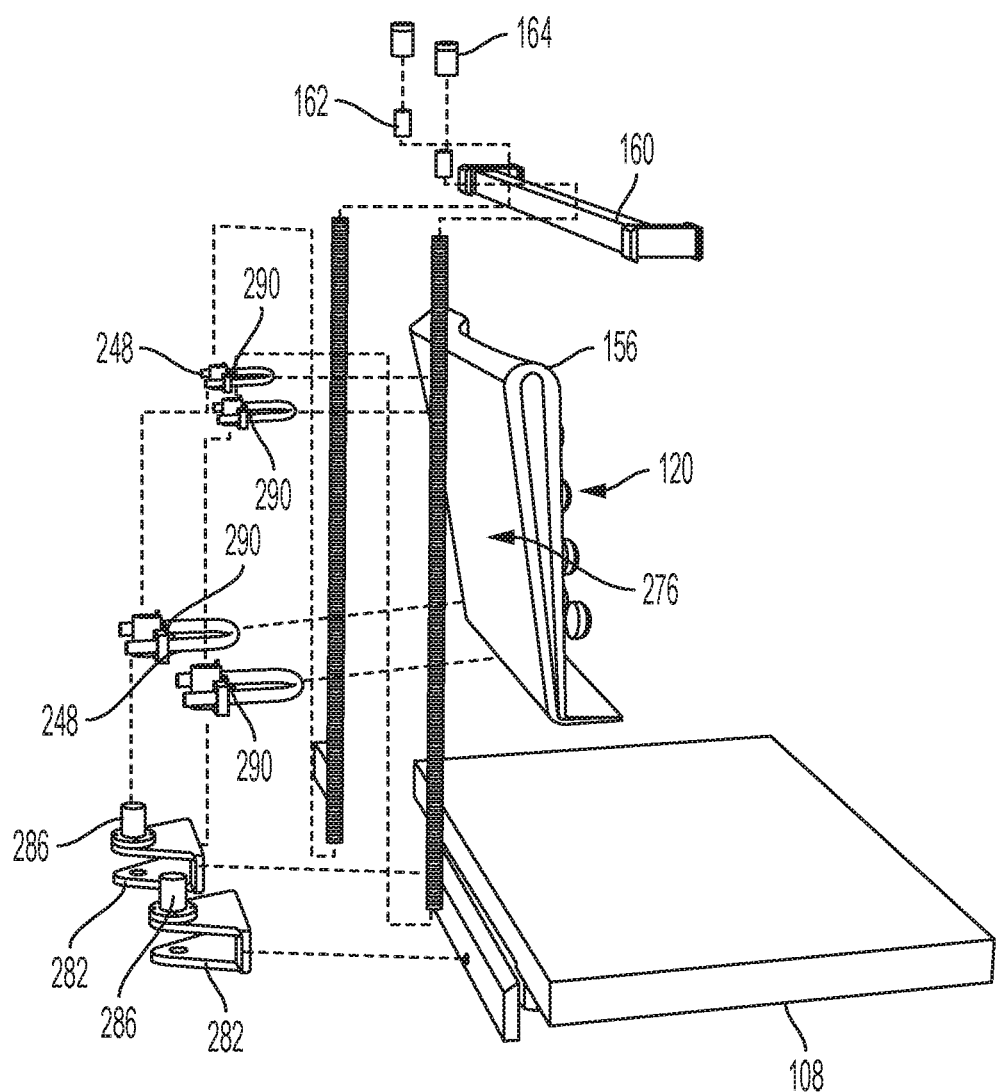
FIG. 6 is an exploded view of the partial seat back of FIG. 5.

FIG. 5 provides a view of the back support 156 components disposed between the back support 156 and the electronics enclosure 122 (FIG. 4), and FIG. 6 provides an exploded view of the components of the back support 156 as described herein. Specifically, a pair of mounting rods 158 couple the back support 156 to the seat 108 and facilitate movement of the back support 156 as further described herein. Each mounting rod 158 is disposed through at least one corresponding bracket 248 coupled to a rear side 276 of the back support 156 opposite from the stethoscope array 120 (FIG. 4). Illustratively, two brackets 248 are utilized for each mounting rod 158 to facilitate stability and security. While the brackets 248 shown differ in size, the brackets 248 may be the same size and shape in other embodiments or may otherwise be different shapes. The brackets 248 may be coupled to the back support 156 using bolts 278, adhesive, overmolding, welding, single-piece manufacturing, other types mechanical fasteners, or other coupling mechanisms known in the art. A bottom portion 280 of each mounting rod 158 is coupled to a seat bracket 282 having a pillow block 286. The seat bracket 282 is coupled to the seat 108 via fasteners 284, although other coupling mechanisms may be utilized.

An upper portion 288 of each mounting rod 158 is disposed through an upper crossbar 160 coupled to the tube frame 104 and couples with a corresponding collar 162 positioned on the side of the upper crossbar 160 facing away from the seat 108. Each mounting rod is operatively coupled to a motor 164, such as a stepper motor, operable to raise or lower the back support 156 so that the stethoscope array 120 is properly aligned with the patient's back during use. Specifically, as shown in FIG. 6, each of the brackets 248 includes a threadable insert 290. The mounting rod 158 is disposed through the insert 290 so that when the motor 164 rotates the mounting rod 158, the mounting rod 158 cooperates with the insert 290 to raise or lower the corresponding bracket 248 and back support 156, either to travel up the mounting rod 158 toward the upper crossbar 160 or down the mounting rod 158 toward the pillow block 286. In other words, when the motor 164 is operable, the mounting rod 158 either rotates in a first direction to raise the corresponding bracket 248 and back support 156 or in a second direction to lower the corresponding bracket 248 and back support 156. Further information related to the stethoscope array and seat back is disclosed and discussed in U.S. Pat. No. 9,208,287 to Waterson, et al., issued on Dec. 8, 2015, the disclosure of which is hereby expressly incorporated by reference.

Referring to FIG. 5, to facilitate appropriate positioning of the back support 156 relative to the patient, an assembly of sensors may be utilized to communicate the position of the back support 156 to the central computer 238 (FIG. 23) as needed. Ideally, a magnetic sensor 292, such as a Hall-effect sensor, may be coupled to an upper portion 288 of each mounting rod 158 or mounting rod collar 162 with a corresponding permanent magnet 294 coupled to the top of the bracket mounted to the back support 156. An additional magnet 296 may be coupled to a vertical post mounted in close proximity and relatively parallel to the corresponding mounting rod 158 or on the corresponding pillow block 286.

Figure 7:
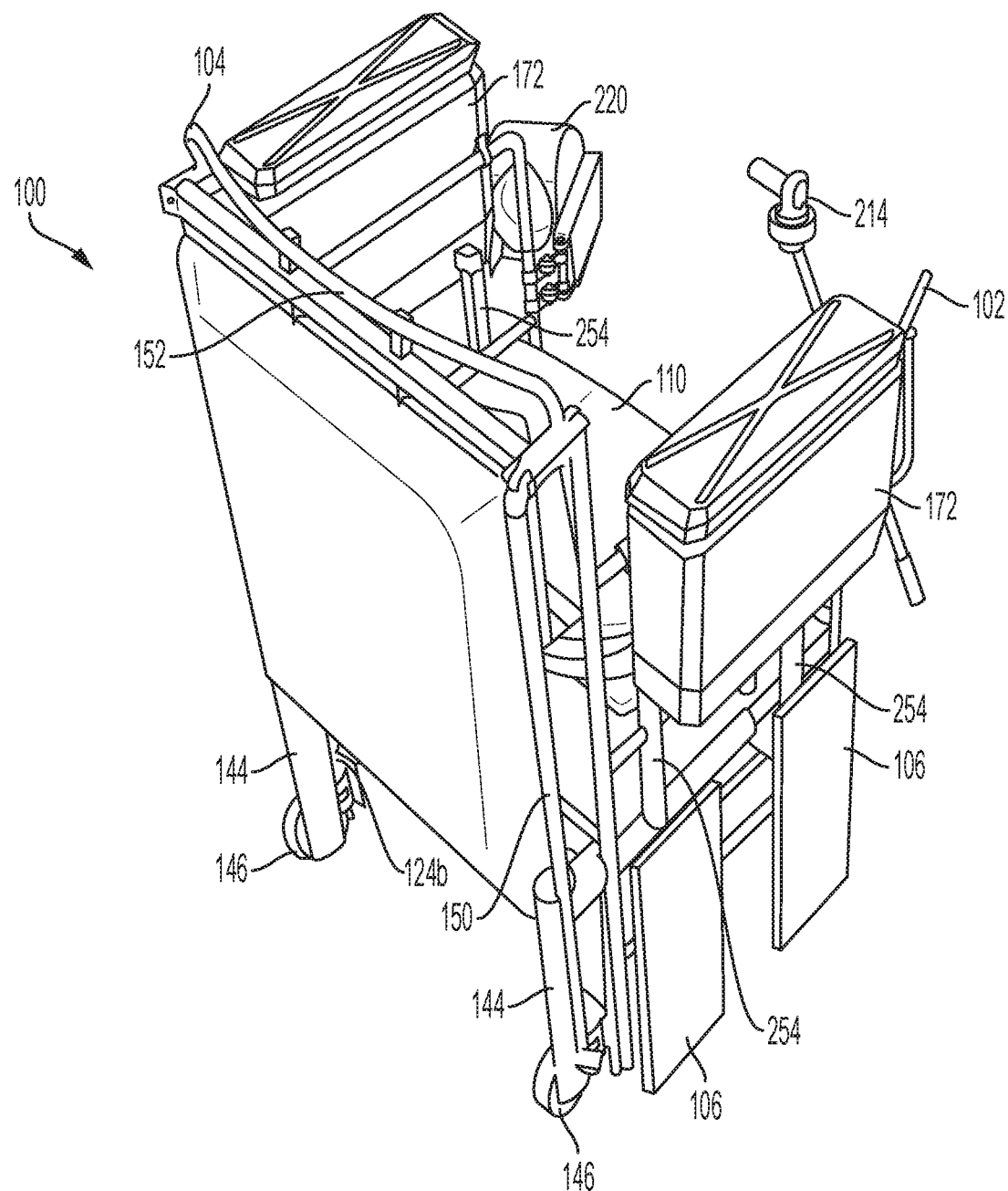
FIG. 7 is a rear perspective view of the medical chair of FIG. 3.

Referring to FIG. 7, the tube frame 104 includes lateral stabilizing legs 254, each lateral stabilizing leg 254 coupled to a lateral stabilizer 106, shown in an undeployed configuration. Illustratively, the medical chair 100 includes four lateral stabilizers 106, two on each side of the medical chair 100. In other embodiments, other numbers of lateral stabilizers 106 may be used. Ideally, an equal number of lateral stabilizers 106 are disposed on either side of the medical chair 100 to provide for equal stabilization. The tube frame 104 is further coupled to rear stabilizers 144, shown in an undeployed configuration. Illustratively, the medical chair 100 includes two rear stabilizers 144. In other embodiments, any number of rear stabilizers 144 may be used. Ideally, the rear stabilizers 144 are equally distributed across the rear of the medical chair 100 to provide for equal rear stabilization.

Figure 8:
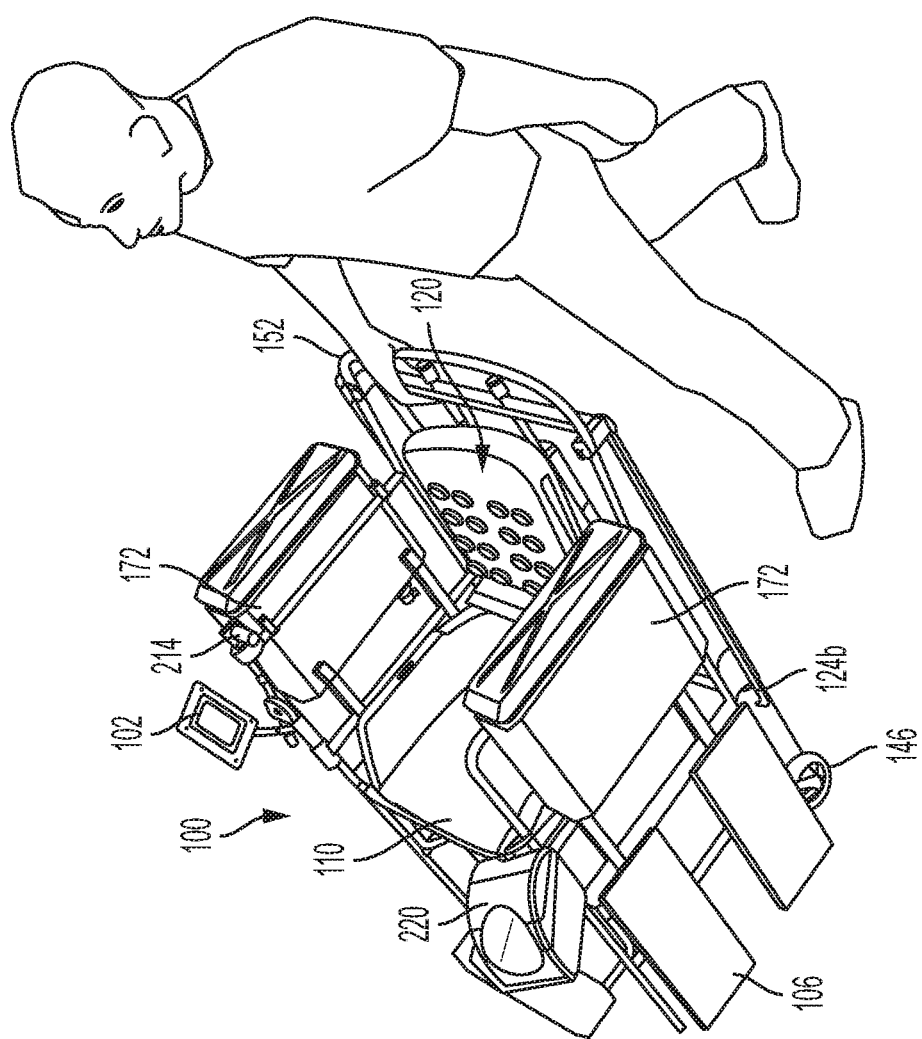
FIG. 8 is an exemplary illustration of user transportation of the medical chair of FIG. 3.

A wheel 146 is mounted to each of the rear legs 124b of the medical chair 100 a predetermined distance above the bottom 148 of the rear legs 124b to allow for transportation of the medical chair 100, as can also be seen in FIG. 3. The tube frame 104 forms a handle 152 to allow a user to tilt the medical chair 100 backwards so that the medical chair 100 is supported by the wheels 146 to facilitate transportation of the medical chair 100 as shown in FIG. 8.

Figure 9:
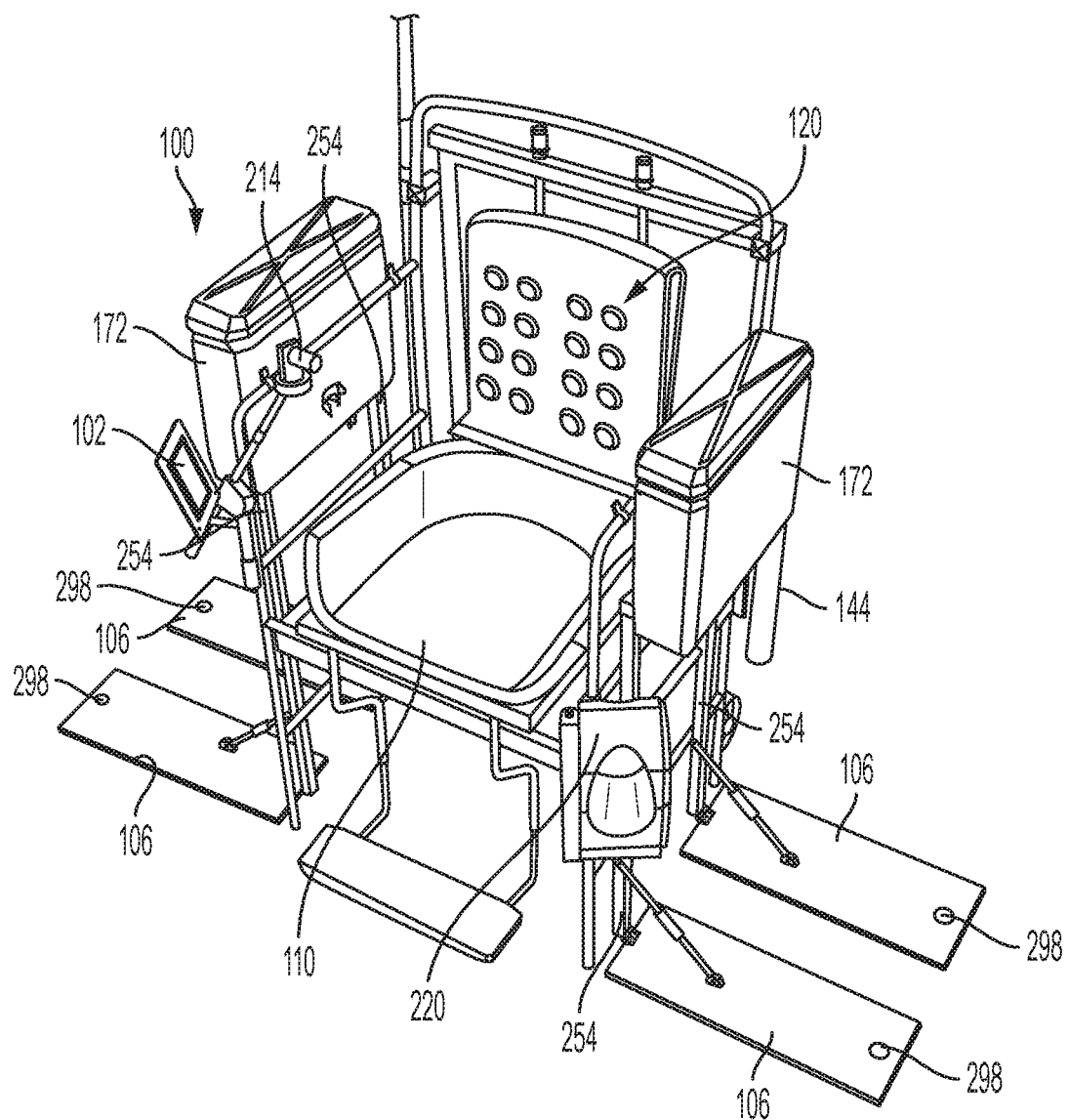
FIG. 9 is a perspective view of the medical chair of FIG. 1, the medical chair in deployed configuration.
Figure 10:
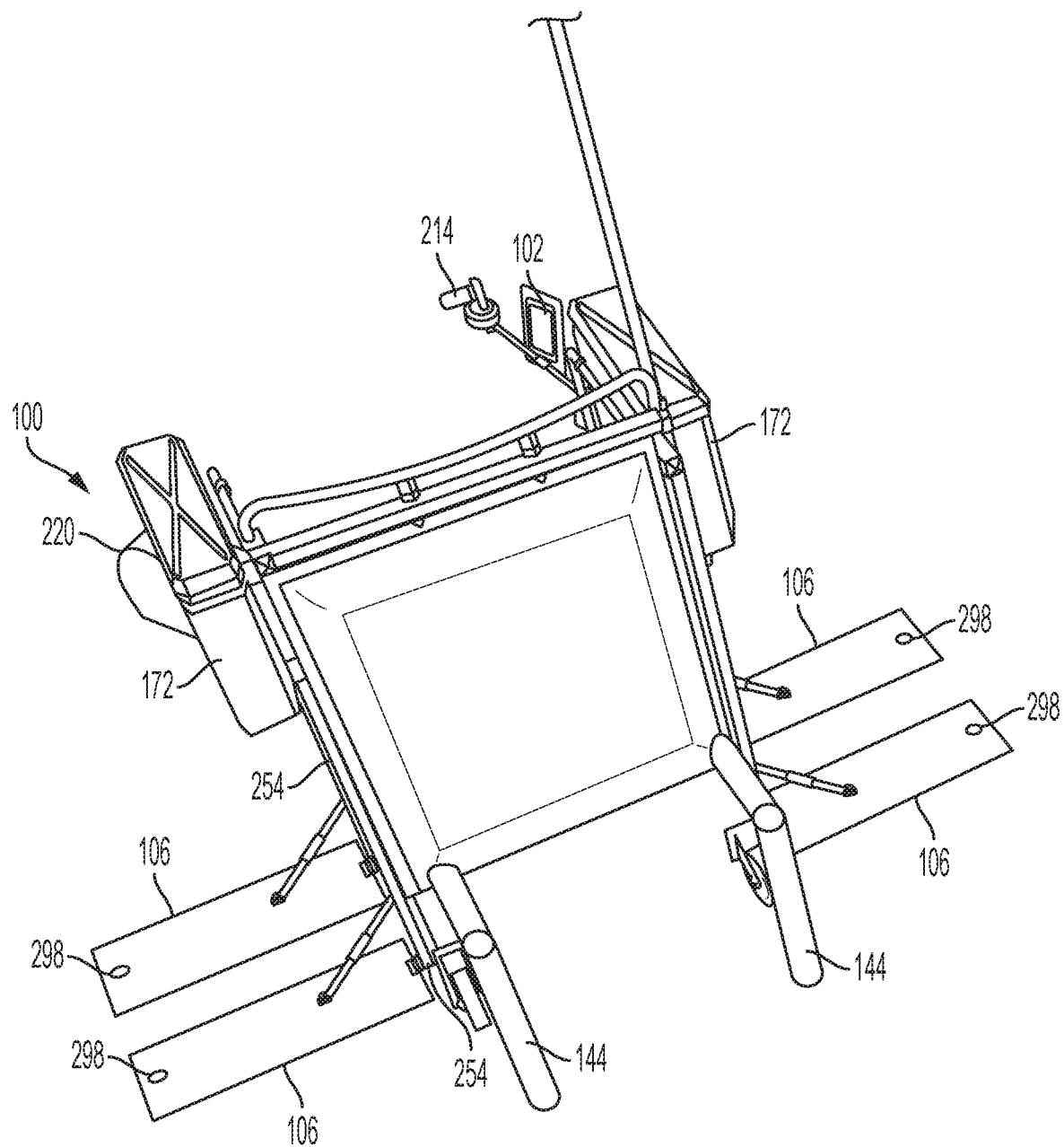
FIG. 10 is a rear perspective view of the medical chair of FIG. 9.

When the medical chair 100 is in use, as shown in FIGS. 9-10, the lateral stabilizers 106 are deployed and lowered to provide extra stability to the medical chair 100 and any patient sitting thereon. The lateral stabilizers 106 may be secured to the surface beneath the medical chair 100 using bolts 298, other fasteners, or other coupling mechanisms. Additionally, the rear stabilizers 144 are deployed and extended to provide extra stability to the medical chair 100 and any patient sitting thereon.

Figure 11:
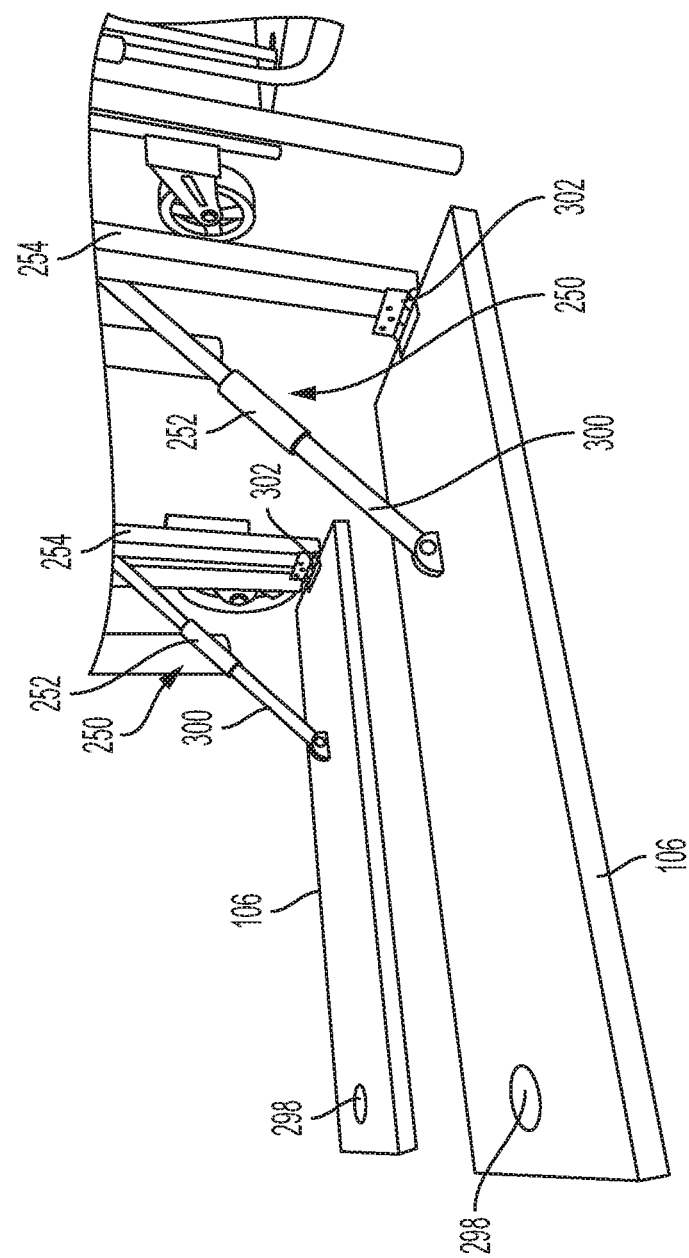
FIG. 11 is a close-up perspective view of a deployed lateral stabilizer of the medical chair of FIG. 9.

As shown in FIG. 11, each lateral stabilizer 106 is rotatably coupled to the corresponding lateral stabilizing leg 254 via a hinge 302 and a stabilizing bar 300. The stabilizing bar 300 is rotatably coupled to each of the corresponding lateral stabilizer 106 and its corresponding lateral stabilizing leg 254 and includes a bar hinge 250. When each lateral stabilizer 106 is lowered from the undeployed configuration to the deployed configuration, the stabilizing bar 300 is straightened along the hinge 250, and a sleeve 252 may be lowered to cover the hinge 250 (FIG. 2) to provide extra stability to the deployed lateral stabilizer.

Figure 12:
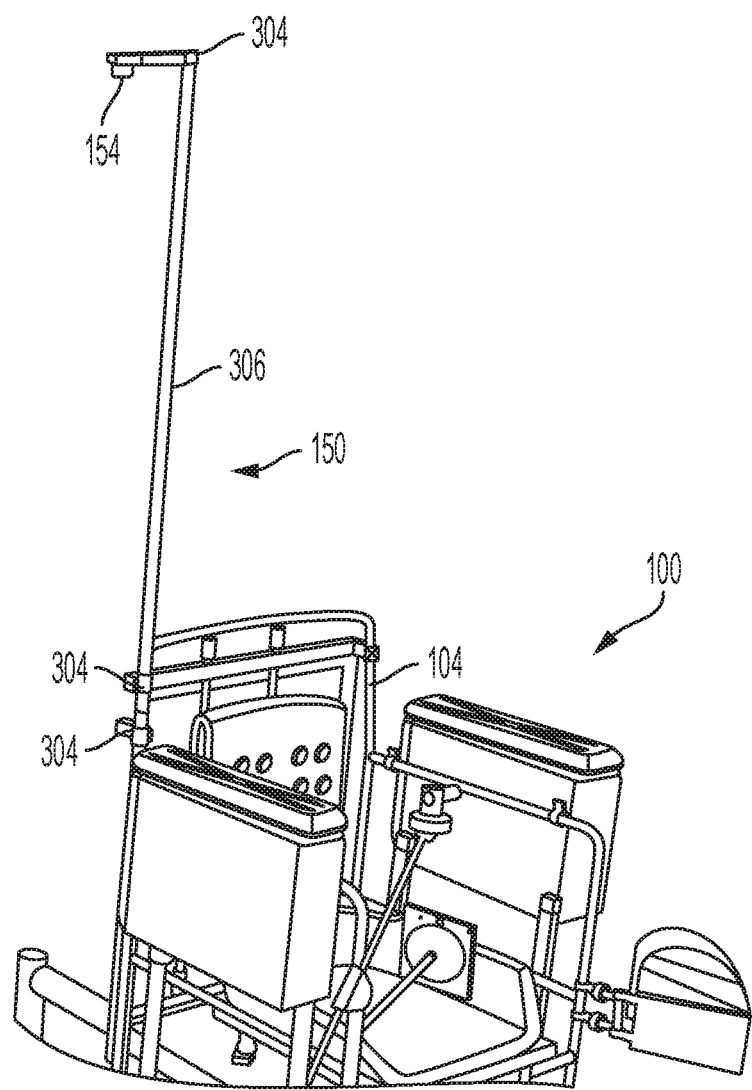
FIG. 12 is a perspective view of a deployed height sensor of the medical chair of FIG. 1.

Now referring to FIG. 12, a height sensor assembly 150 is coupled to the tube frame 104. The height sensor assembly includes a plurality of hinges 304 so that the height sensor assembly 150 can rotate from an undeployed configuration (FIG. 7) to a deployed configuration as illustrated. In some embodiments, the height sensor assembly is directly coupled to the tube frame 104 by one of the hinges 304. In other embodiments, the height sensor assembly is coupled to the tube frame 104 via welding, brackets, or other coupling mechanisms with a hinge positioned along a body 306 of the height sensor assembly 150 to facilitate movement of the height sensor assembly 150 from the undeployed configuration (FIG. 7) to the deployed configuration. When deployed, the height sensor assembly 150 is ideally positioned so that an adult can stand underneath the height sensor assembly 150. For example, the height sensor assembly 150 may stand between about 7' and about 8' from a surface beneath the medical chair 100.

Figure 13:
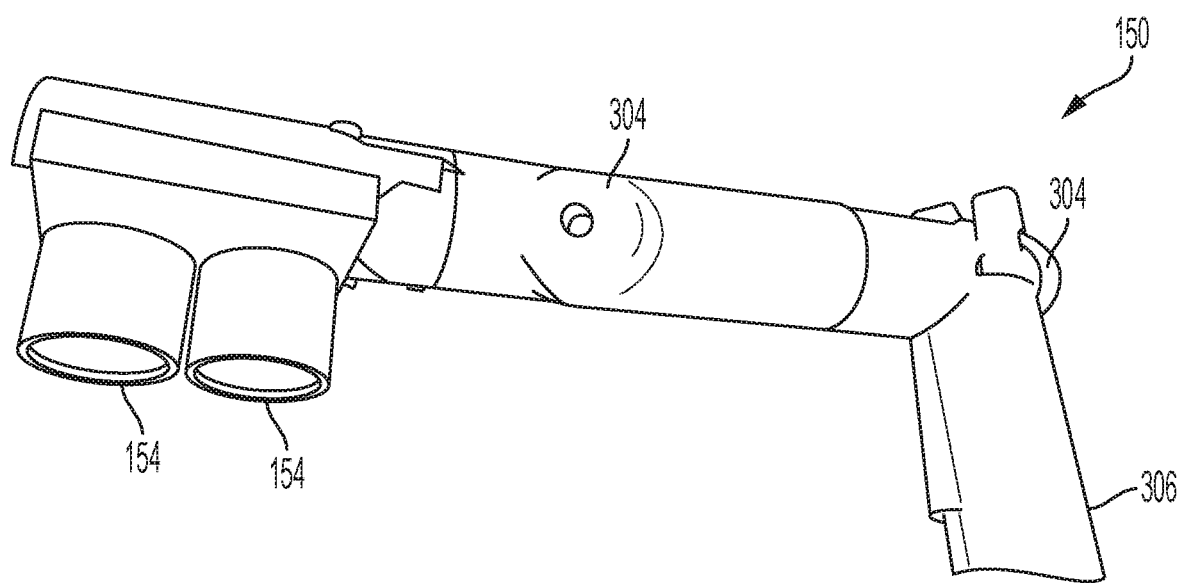
FIG. 13 is a close-up perspective view of the deployed height sensor of FIG. 12.
Figure 16:
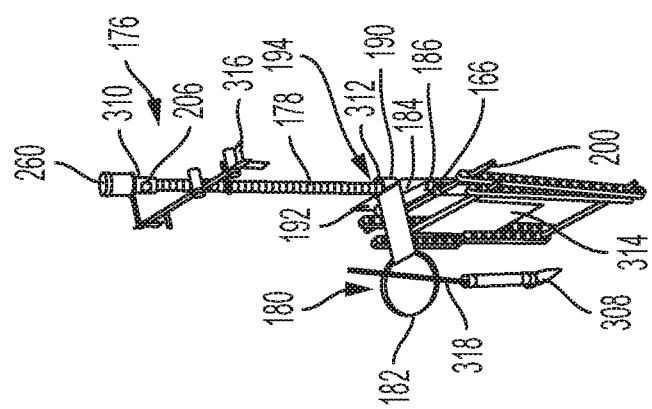
FIG. 16 is a perspective view of the instrument assembly of FIG. 15.

Referring additionally to FIG. 13, the height sensor assembly 150 includes at least one ultrasonic sensor 154 configured to receive and/or transmit an ultrasonic signal under the control of the central computer 238 (FIG. 23) to measure the height of a patient standing under the ultrasonic sensor 154. In some embodiments, as illustrated, the height sensor assembly 150 includes two ultrasonic sensors 154, wherein one of the two ultrasonic sensors 154 is configured to receive an ultrasonic signal, while the other of the two ultrasonic sensors 154 is configured to transmit an ultrasonic signal.

The ultrasonic signal is transmitted from the ultrasonic sensor 154 to the top of the patient's head, wherein the ultrasonic signal reflects from the patient's head to be received by the same ultrasonic sensor 154 or an additional ultrasonic sensor 154. A circuit 155 (FIG. 23) of the height sensor assembly measures the delay between the transmittal of the ultrasonic signal and the reception of the reflected ultrasonic signal to calculate the height of the patient. The circuit is communicatively coupled to the central computer 238 (FIG. 23) so that the measured height of the patient can be communicated by the circuit to the central computer 238 for further transmittal and storage.

Referring again briefly to FIG. 4, the tube frame 104 defines two handrails 170, one disposed on each side of the seat 108. Each handrail 170 supports a docking station 172 as described further herein. As shown, the docking stations 172 are coupled to the corresponding handrail 170 using a pair of brackets 174. In some embodiments, a fewer number or a greater number of brackets may be utilized. In other embodiments, other coupling mechanisms may be used, including adhesive, overmolding, welding, other mechanical fasteners, single-piece manufacturing, and other coupling mechanisms as known in the art.

As illustrated in FIG. 14, each docking station 172 defines a chamber 204 housing a plurality of instrument assemblies 176 for storing and delivering an instrument 308 to the patient during use of the medical chair 100. Illustratively, each docking station 172 includes four instrument assemblies 176. In other embodiments, each docking station 172 may include a greater number of instrument assemblies or a fewer number of instrument assemblies as needed to compile the medical information needed to diagnose and treat the patient. The docking stations 172 may include the same number or a differing number of instrument assemblies. The instruments may include, but are not limited to, a thermometer, an oximeter, a dermascope, an otoscope, a chest piece stethoscope, or a glucose monitor. A plurality of apertures 198 (FIG. 17) is defined by a bottom face 310 of the docking station for each instrument assembly 176 so that the instrument assembly 176 is configured to lower the corresponding instrument 308 through the corresponding aperture 198 for access and use by the patient as further discussed herein.

Figure 17:
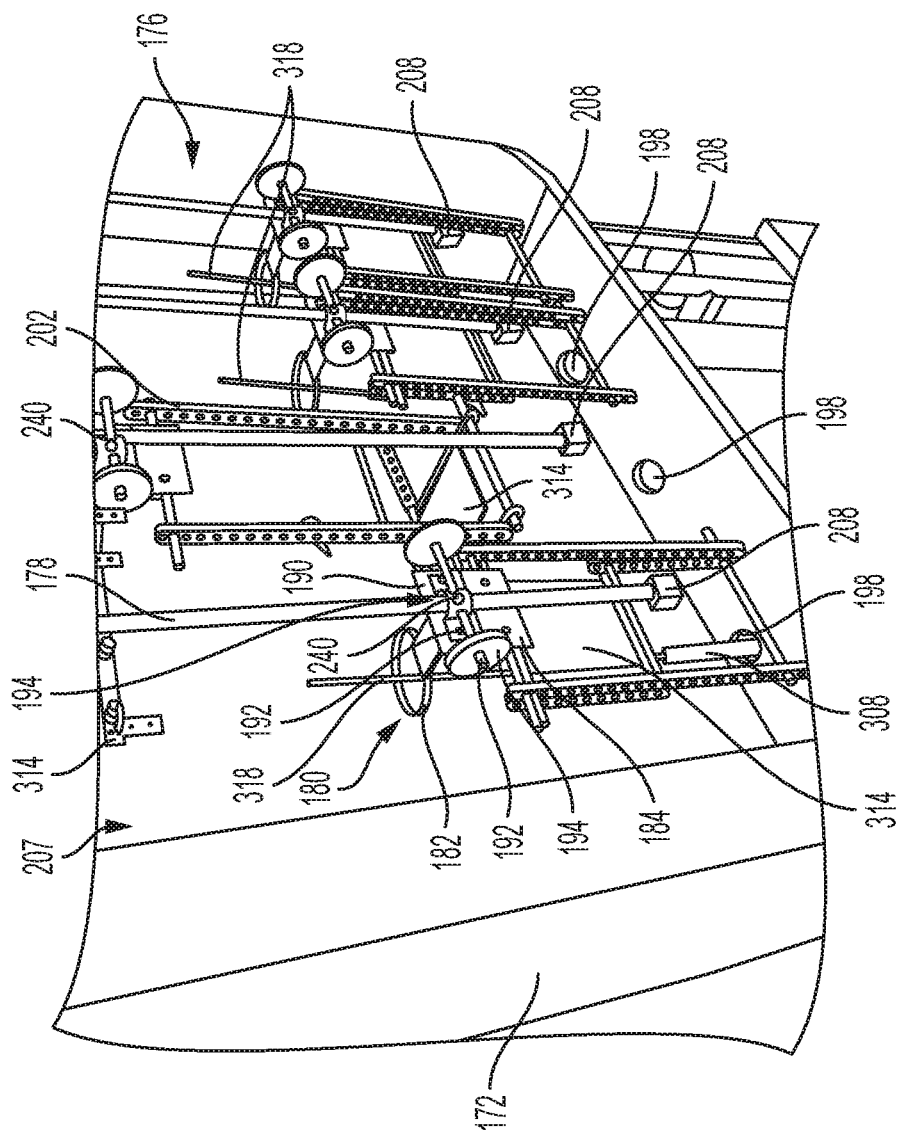
FIG. 17 is a close-up rear perspective cross-sectional view of the instrument docking station of FIG. 14.

As shown in FIGS. 15-18, the instrument assembly 176 may be secured to an inside surface 196 of the docking station 172 by bracket 316, the instrument assembly including a delivery rod 178 coupled to a pillow block 208 positioned in the chamber 204 near the aperture 198 (FIG. 17). Opposite from the pillow block 208, the delivery rod is coupled to a rod collar 310 and a motor 260, such as a stepper motor. The instrument assembly 176 further includes an instrument support, or instrument guide 180, having a guide portion 182 and a bracket portion 184. The guide portion 182 is configured to receive and support the corresponding instrument 308. The bracket portion 184 includes a compartment 186 for supporting a magnetic sensor 188, such as a Hall-effect sensor. A magnet 206 is mounted at the top of the instrument assembly 176 near or on the rod collar 310 and at the bottom of the instrument assembly 176 near or on the pillow block 208. The compartment 186 may also serve as a mounting point for any load bearing or data cables coupled to the instrument, as well as any connector terminals wired to a microcontroller 258 (FIG. 23) in contact with the central computer 238 (FIG. 23) and associated with each instrument. Opposite of the guide portion 182, the bracket portion 184 of the instrument guide 180 is coupled to a roller bracket 190 via mechanical fasteners, such as screws 192. In other embodiments, the roller bracket 190 and the bracket portion 184 may be coupled via other coupling methods known in the art as described throughout the disclosure.

The roller bracket 190 and the bracket portion 184 define a through-hole 194 configured to receive the delivery rod 178 to couple the instrument guide 180 and the roller bracket 190 to the delivery rod 178. Illustratively, a threadable insert 312 is disposed within the through-hole 194 formed between the roller bracket 190 and the bracket portion 184 to facilitate movement of the instrument guide 180 upward toward the motor 260 or downward toward the aperture 198 as needed. In other words, when the motor 260 is in operation, the motor 260 rotates the delivery rod 178 so that the delivery rod 178 cooperates with the insert 312 to raise or lower the roller bracket 190 and the instrument guide 180. The magnetic sensor 188 and the magnets 206 cooperate to locate the position of the instrument 180 along the delivery rod 178. The position of the instrument guide 180 is communicated to the central computer 238 (FIG. 23) as needed, and the central computer 238 (FIG. 23) may enable the motor 260 to raise or lower the instrument guide 180 as needed or otherwise shut off the motor 260.

Figure 18:
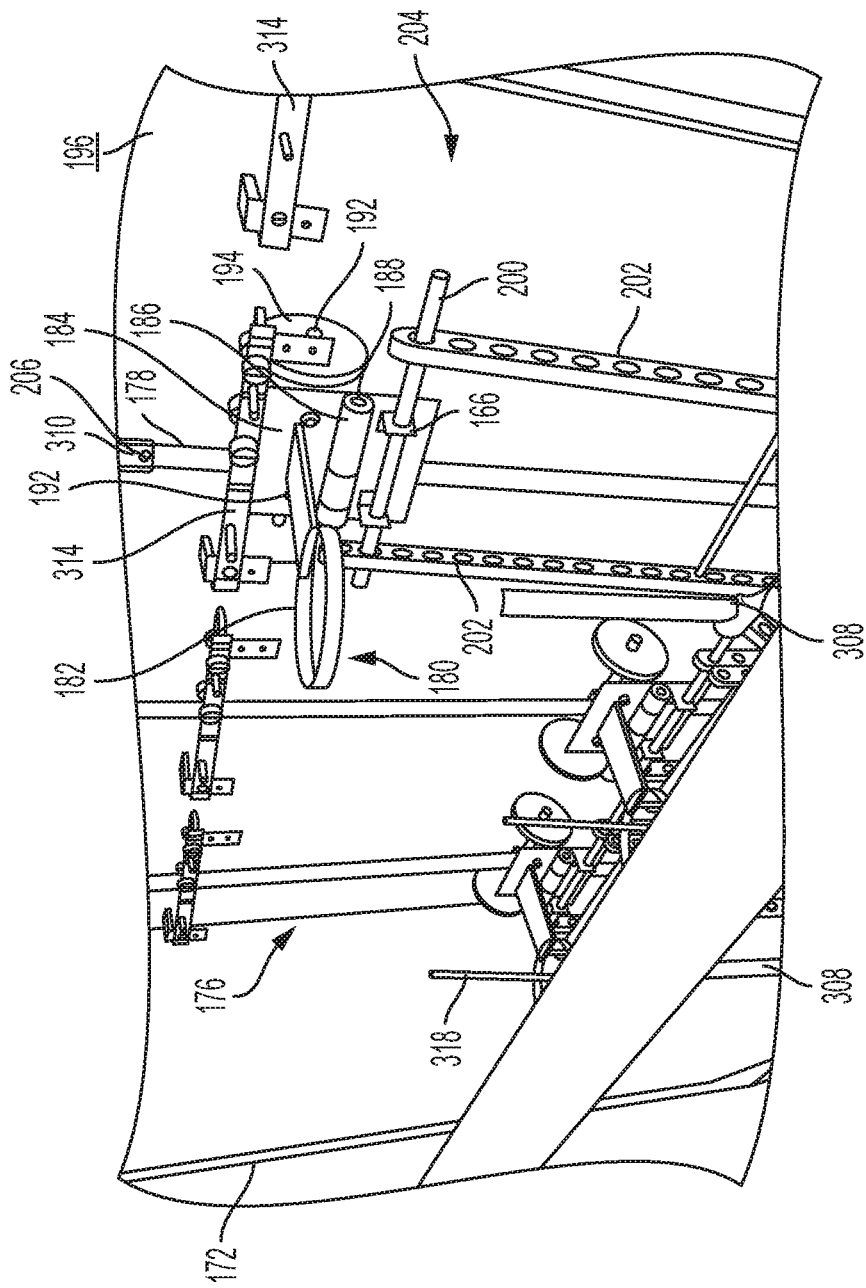
FIG. 18 is a close-up perspective cross-sectional view of the instrument docking station of FIG. 14.

Now referring to FIGS. 17-18, the roller bracket 190 may include an axle 192 extending latitudinally from the roller bracket 190, with a wheel 194 rotatably positioned on each end of the axle 192. The wheels 194 contact an inside surface 196 of the docking station 172 to act as a guide for the instrument guide 180 during use and prevent the instrument guide 180 from rotating with the delivery rod 178. A spring-loaded tail device 240 extends beyond the axle 192 between the wheels 194 to ensure the wheels 194 of the roller bracket 190 are pressed firmly against the inside surface 196 of the docking station 172 while still allowing rotation of the wheels 194.

Referring again to FIGS. 14-18, the bracket portion 184 of the instrument guide 180 further includes a bracket assembly 166 positioned beneath the compartment 186 and configured to receive a cantilever rod 200. The cantilever rod 200 extends beyond the bracket assembly 166 to couple to a pair of cantilever shafts 202 on each end of the cantilever rod 200, requiring the cantilever shafts 202 to move as the shaft collar 180 is raised or lowered along the delivery rod 178. The cantilever shafts 202 are operably coupled to a cantilever cover 314 so that movement of the cantilever shafts 202 correspondingly opens or closes the cantilever cover 314. The position of the cantilever cover 314 therefore corresponds with the position of the instrument guide 180 so that the cantilever cover 314 opens as the instrument guide 180 lowers toward the aperture 198, allowing the instrument 308 to bypass the cantilever cover 314 and be presented through the aperture 198 for access by the patient. As the instrument guide 180 is raised into the chamber 204 in a direction away from the aperture 198, the cantilever cover 314 closes, preventing a patient or bystander from accessing the instrument 308 through the aperture 198 when unauthorized.

When the cantilever cover 314 is retracted and the instrument 308 is lowered near to or through the aperture 198, the patient may retrieve the instrument 308, the instrument ideally coupled to the instrument assembly 176 with a cable 318 that secures the instrument to the instrument assembly 176 while providing the patient with flexibility during use. When the cantilever cover 314 is in the closed position, the patient is not provided access to the chamber 204 or the instrument assemblies 176 contained therein. Any excess length of cable 318 may be retracted into and stored in a trough with storage of the corresponding instrument 308. The arrangement and operation of the delivery rod 178, the roller bracket 190 and its corresponding components, the magnetic sensor 188, and the cantilever assembly, including the cantilever rod 200, the cantilever shafts 202, and the cantilever cover 314, allow for operation without use of winch motors, pulleys, counter weights, or mechanical proximity switches.

Figure 19:
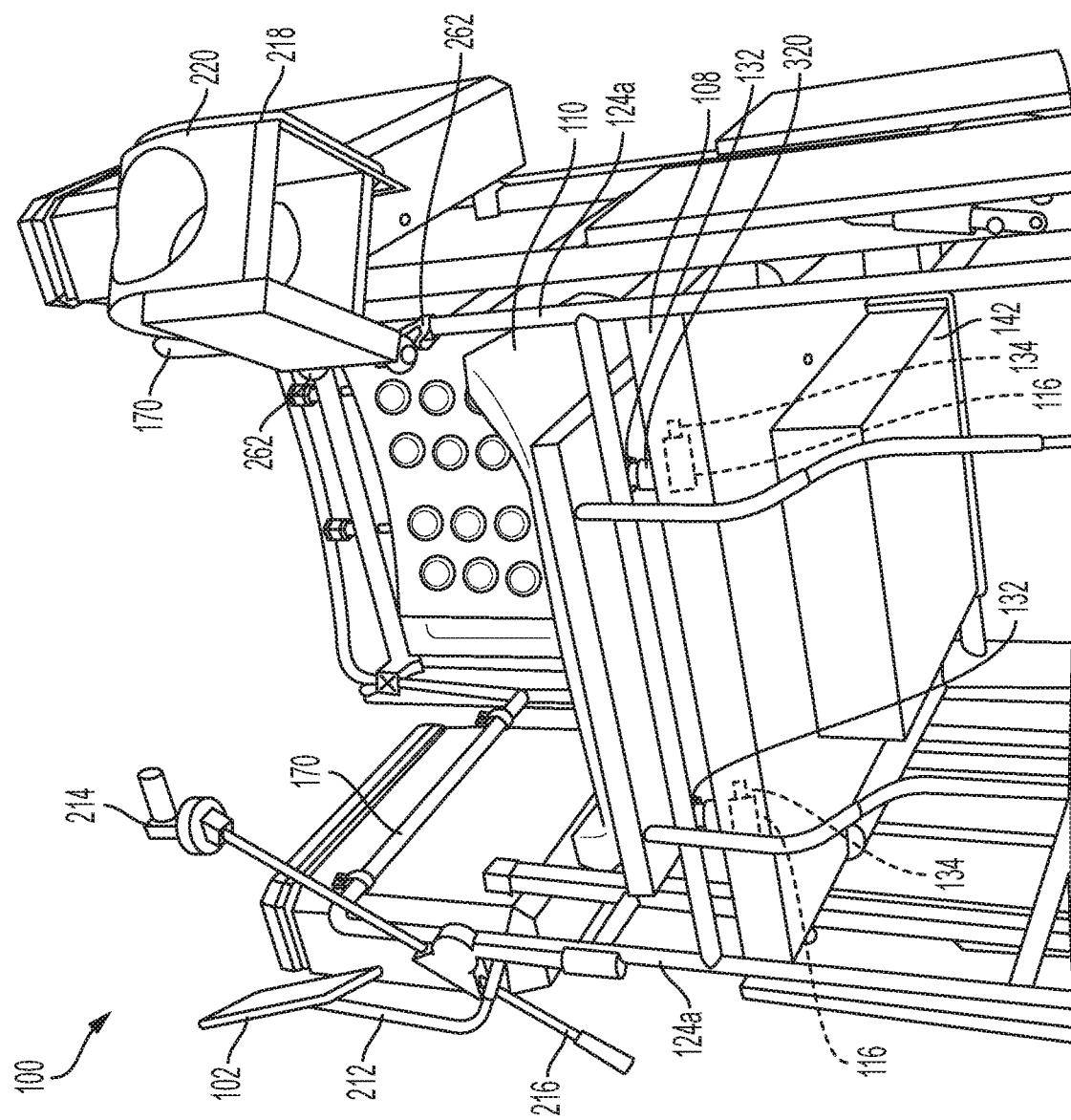
FIG. 19 is a bottom-up perspective view of a seat of the medical chair of FIG. 1.

Now referring to FIG. 19, a weighted boom 212 supporting the patient user interface 102 is rotatably supported by one of the handrails 170 so that the boom 212 is capable of being moved toward and away from the seat 108 for convenient placement of the boom 212 mounted patient user interface 102 as desired by the patient. A spirometer 214 is mounted to a spirometer boom 216 supported by one of the handrails 170, so that the spirometer boom 216 is capable of being moved to a convenient position for the patient to access the spirometer 214 as needed. The spirometer 214 is operatively coupled to the central computer 238 (FIG. 23) for measurement, storage, and transmission of data. A cuff support 218 is rotatably coupled to one of the front legs 124a and supports a blood pressure cuff 220. A pair of hinges 262 or other rotatable fasteners couples the cuff support 218 to the leg 124a to allow the patient to position the cuff support 218 and blood pressure cuff 220 near the patient for use or away from the patient when not in use. The central computer 238 (FIG. 23) is operatively coupled to the blood pressure cuff 220 to measure, store, and transmit the blood pressure of the patient.

Figure 20:
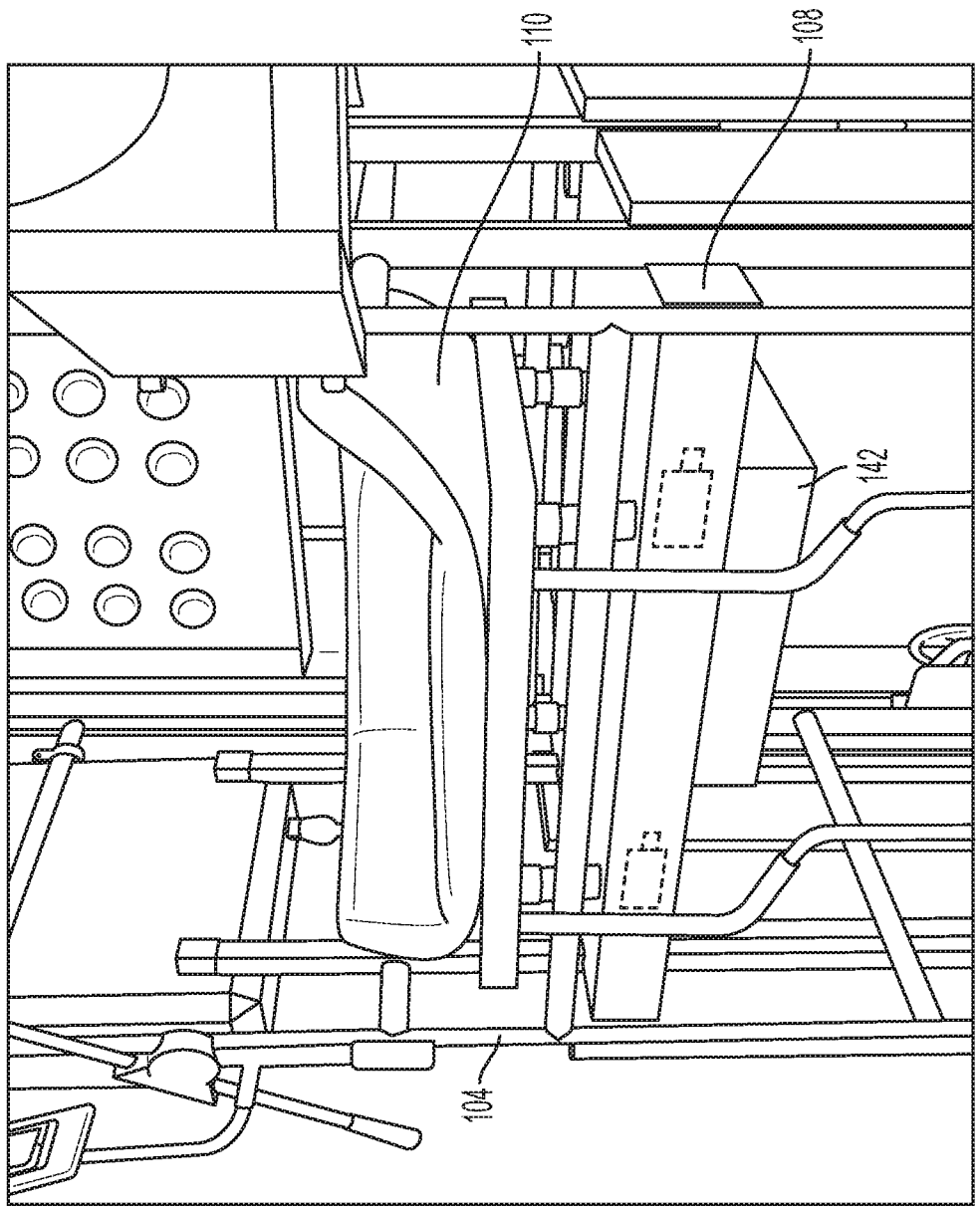
FIG. 20 is a close-up perspective view of the seat of the medical chair of FIG. 1

Now referring to FIGS. 19-20, the tube frame 104 supports the seat 108, the seat 108 supporting a seat scale 110 to support the patient and measure the patient's weight. As seen from the exploded view of the seat assembly in FIG. 21, a plurality of pins 126 having compression spring sleeves 128 are coupled to a bottom surface 130 of the seat scale 110. Spacers 320 are positioned between the seat scale 110 and the seat 108 to support the seat scale 110 above the seat 108, the spacers 320 each having an aperture 322 to receive the corresponding pin 126. While the illustrative embodiment includes a two stacked spacers 320 per pin 126, other embodiments may include a fewer number of spacers 320, a greater number of spacers 320, or spacers of different size and/or shape, as long as the spacers 320 are configured to support and position the seat scale 110 a predetermined distance from the seat 108 so that the pins 126 do not contact a corresponding weight sensor 116 as further described herein.

A plurality of load cells, or weight sensors 116, are disposed within a body 322 of the seat 108. A plurality of holes 210 corresponding with the pins 126 are provided in the seat 108 to allow the pins 126 to selectively contact the weight sensors 116. The holes 210 may be lined with a polymer, such as PTFE, or other substrate to enable near frictionless movement of the seat scale 110 during use. When a patient sits on the seat scale 110, the force of gravity acting on the patient forces the seat scale 110 in a downward motion, guiding the pins 126 into the holes 210 to contact the weight sensors 116. The force of the contact between the pins 126 and the weight sensors 116 is measured by the weight sensors 116 and communicated to the central computer 238 (FIG. 23) for storage and transmission.

Referring again to FIGS. 19-20, a magnet 132 is further disposed beneath the seat scale 110 adjacent to each of the plurality of pins 126 and aligned with a magnetic sensor 134, such as a Hall-effect sensor, mounted within the seat 108. The magnetic sensors 134 and the magnets 132 cooperate to determine the position of the seat scale 110. In other words, if the seat scale 110 receives an even load to facilitate accurate weight measurement, the magnetic sensors 134 and the magnets 132 are aligned so that the analog voltage output of each of the magnetic sensors 134 are substantially similar or identical to each of the other magnetic sensors 134. The magnetic sensors 134 may be communicatively coupled to the central computer 238 (FIG. 23) to transmit and receive data as needed. As such, the seat scale 110 is assembled so that no cables or wires are required to attach to the seat scale 110 so that the seat scale 110 is removable from the seat 108 as desired.

Figure 21:
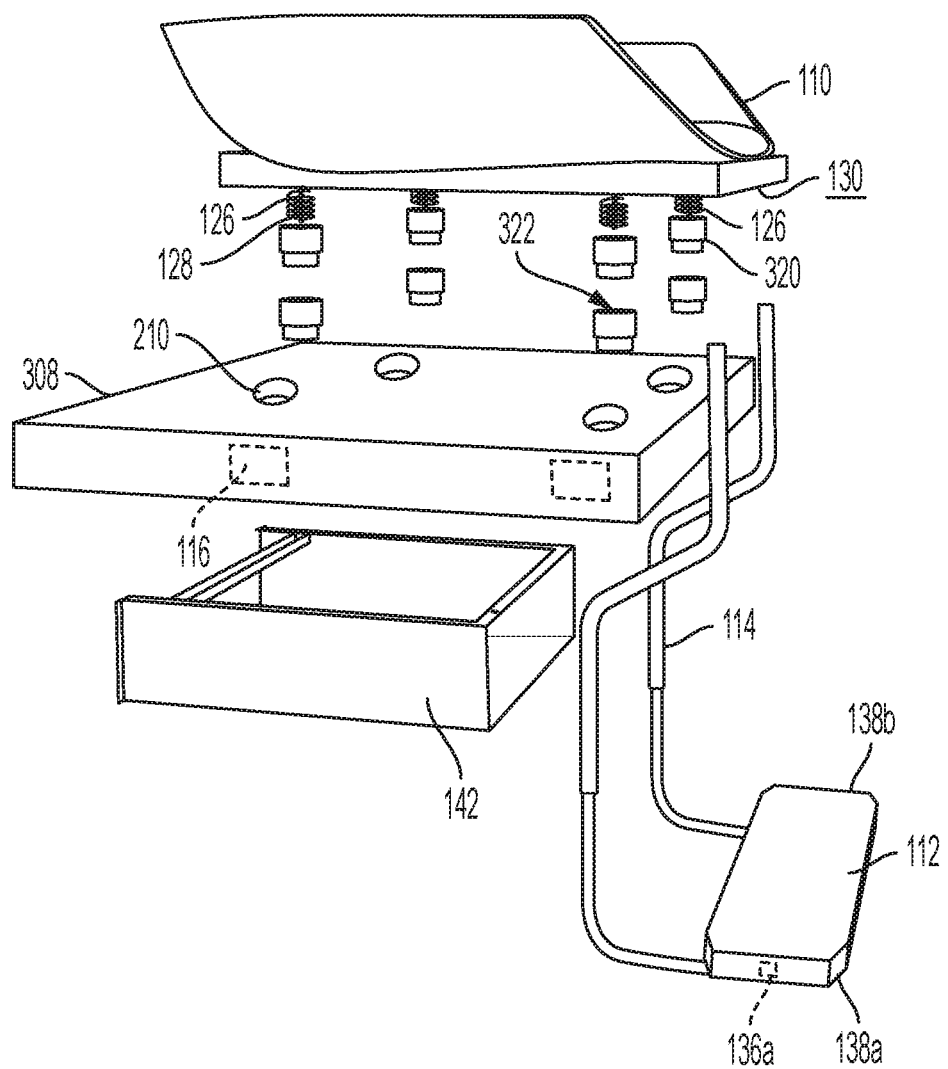
FIG. 21 is an exploded view of the seat of FIG. 20.
Figure 22:
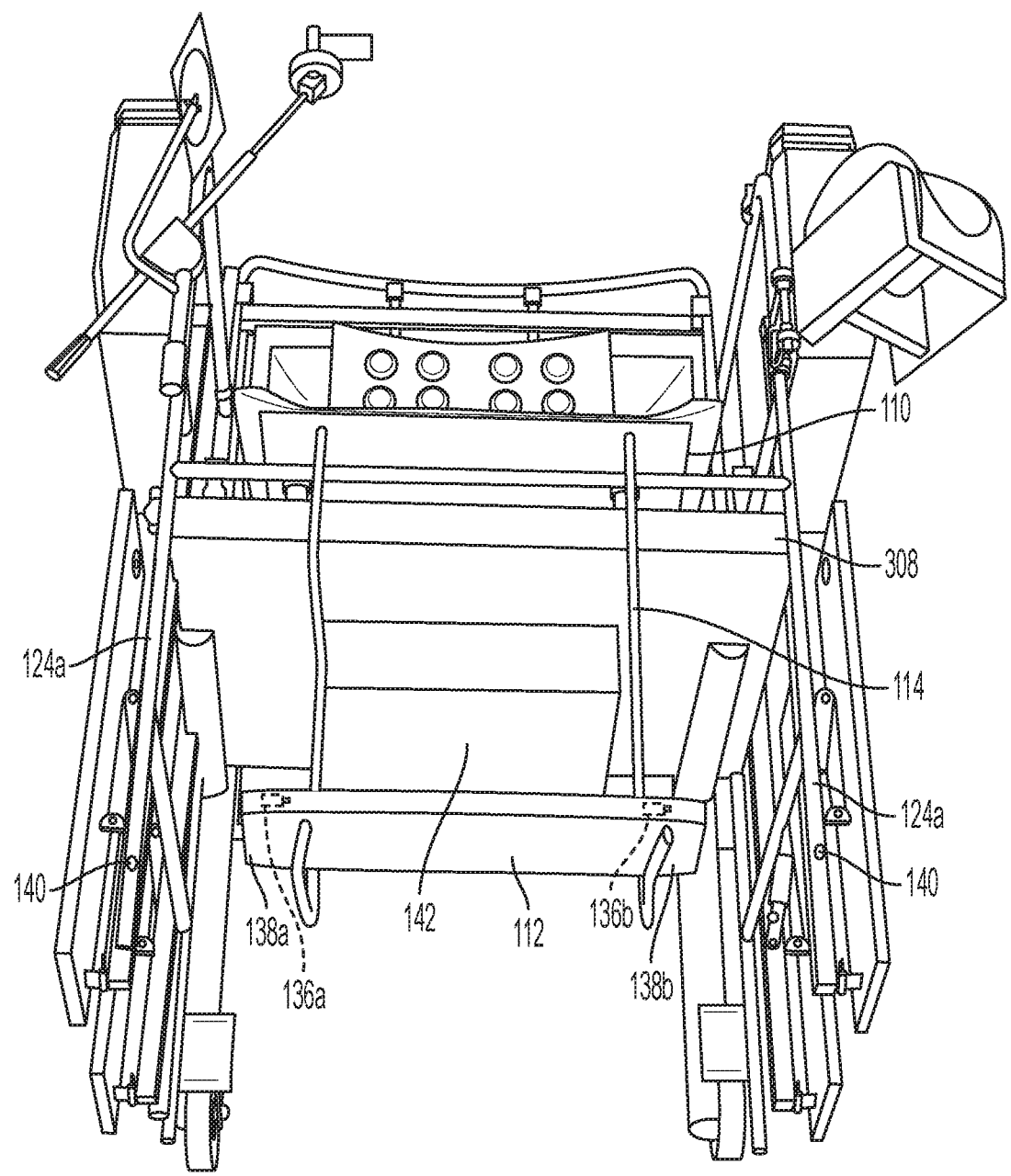
FIG. 22 is a bottom-up perspective view of the medical chair of FIG. 1.

As shown in FIGS. 21-22, a footrest 112 is coupled to the seat scale 110 via attachment members 114, so that the patient may position his or her feet on the footrest 112 to obtain a more accurate weight measurement as described further herein. The attachment members 114 curve inward toward the seat 108 between the seat scale 110 and the foot rest 112 to provide an ergonomic shape and to facilitate an accurate weight measurement by centering gravity beneath the patient.

The footrest 112 includes a first magnet 136a at a first end 138a of the footrest 112 and a second magnet 136b at a second end 138b of the footrest 112. A magnetic sensor 140 is disposed on each of the front chair legs 124a, each of the magnetic sensors 140 corresponding to one of the footrest magnets 136 of the footrest 112. The magnetic sensors 140 and the magnets 136 cooperate to ensure an even load is present on the footrest 112 during weight measurement of a patient. In other words, if the footrest 112 receives an even load to facilitate accurate weight measurement, the magnetic sensors 140 and the magnets 136 are aligned so that the analog voltage output of each of the magnetic sensors 140 are substantially similar or identical to the other magnetic sensor 140. The magnetic sensors 140 may be communicatively coupled to the central computer 238 (FIG. 23) to transmit and receive data as needed.

Referring again to FIGS. 19-23, a seat drawer 142 is mounted below the seat 108, the seat drawer 142 configured to store equipment needed for operation of the medical chair 100 as further described herein. For example, referring specifically to FIG. 23, the seat drawer 142 may contain a power supply 266, a backup power supply 268, and a relay 264 to determine when an internal power supply is needed, or if power is being supplied by an outside source to provide power to any control and data processing electronics and medical instruments included with or otherwise coupled to the medical chair 100. An accelerometer 270 may also be disposed within the seat drawer 142 to determine whether the chair is positioned on a level surface as discussed further herein. A Bluetooth® module 272 may be disposed within the seat drawer 142 to transmit or receive Bluetooth® signals as needed. The central computer 238 is further stored within the seat drawer 142 and includes Wi-Fi or wireless Internet technology and 4G cellular modules for connecting to the Internet. Other embodiments may include technology for wired Internet connections, 5G cellular modules, or other technology providing for remote data transfer as known in the art.

Figure 23:
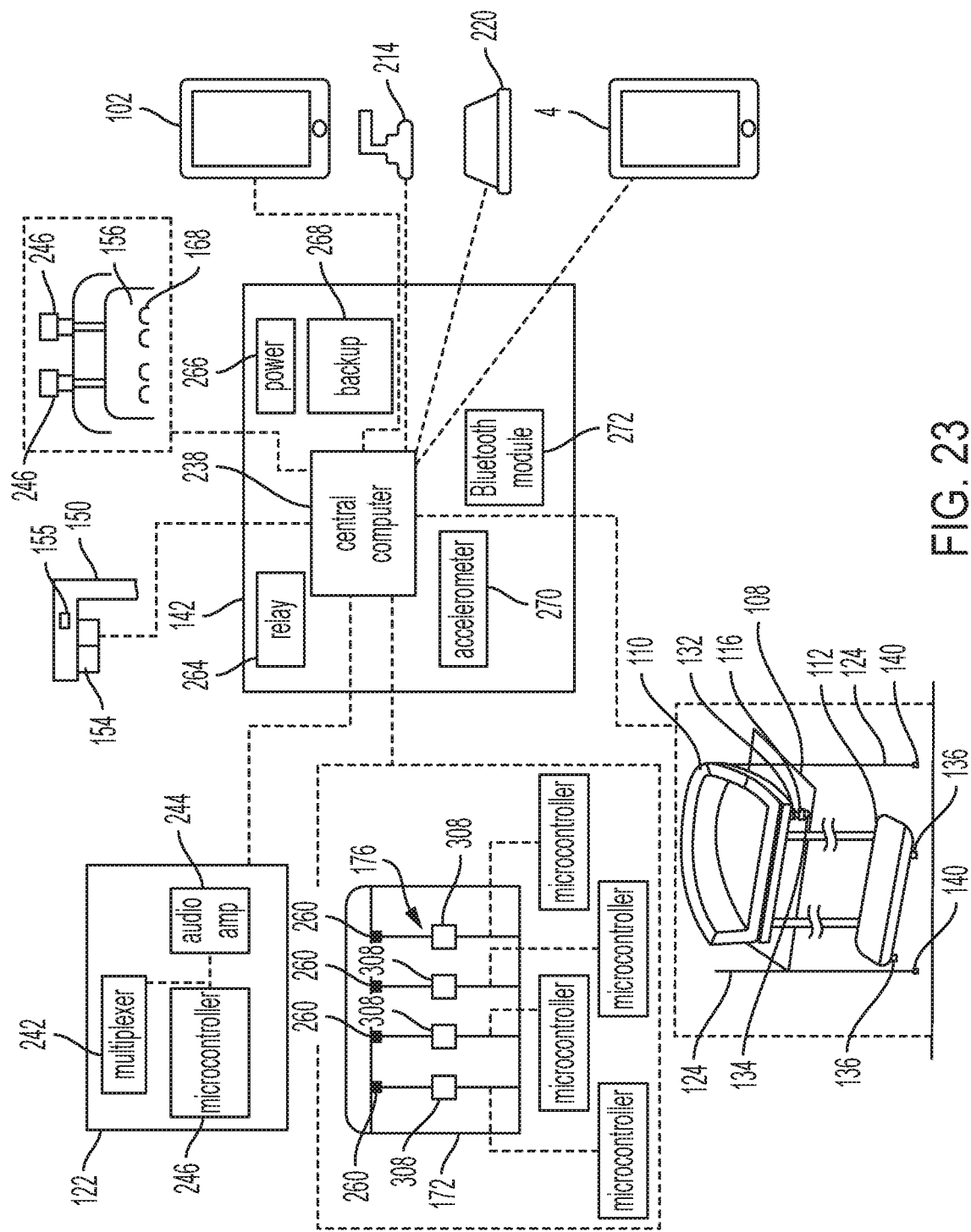
FIG. 23 is a schematic view of the electronic components of the medical chair of FIG. 1.

Referring specifically to FIG. 23, the central computer 238 contained within the seat drawer 142 receives data from the patient user interface 102, the spirometer 214, the blood pressure cuff 220, the instruments 308 contained within the docking station 172, the audio amplifier 244 contained within the electronics enclosure 122 of the chair back 118, the magnetic sensors 134, 136, 140, 188, the electric sensors 168 of the stethoscope array 120, the weight sensors 116, and the at least one ultrasonic sensor 154 of the height sensor 150 to communicate the data with the medical practitioner user interface 4 for diagnostic and treatment purposes. Similarly, the medical practitioner user interface 4 is configured to communicate with the central computer to remotely operate the chair, i.e., to position the back support 156, operate the delivery rod 178 of one of the plurality of instrument assemblies 176, operate the seat scale 110, operate the at least one ultrasonic sensor 154 of the height sensor 150, operate the blood pressure cuff 220, or conduct further action to ensure a thorough exam.

Referring again to FIGS. 7-11, the medical chair 100 as described herein may be positioned in a semi-permanent location, such as an unmanned walk-in clinic, a temporary medical clinic, or a permanent manned clinic. An illustrative environment in which the medical chair 100 may be installed is disclosed and described in U.S. Pat. No. 10,366,205 to Waterson, et al., issued on Jul. 30, 2019, the disclosure of which is hereby expressly incorporated by reference. In such an environment, the medical chair 100 may be operatively coupled to an outside power source, such as a wired outlet, to provide outside power to the various components of the medical chair 100 as described above. For proper operation, the medical chair 100 must be placed on an even surface. Once positioned on an even surface as determined by the accelerometer 270 (FIG. 23), the lateral stabilizers 106 and the rear stabilizers 144 are deployed to stabilize the chair 100 as described above and may be bolted or otherwise semi-permanently coupled to the floor, ground, or other surface beneath the medical chair 100 if desired, however, once the lateral stabilizers 106 and the rear stabilizers 144 are deployed, tipping or moving of the chair becomes difficult.

Once the medical chair 100 has been positioned and secured via deployment of the lateral stabilizers 106 and the rear stabilizers 144, the seat scale 110 may be tested using a standard weight with a known weight measurement. If the seat scale 110 needs to be recalibrated, the patient user interface 102 or a service interface (not shown) may be used to recalibrate the service tablet. The central computer 238 (FIG. 23) may be programmed to test all of the instruments in the docking stations 172, the spirometer 214, the stethoscope array 120, and the blood pressure cuff 220 to ensure they are working properly when requested by the patient user interface 102 or the service interface. The patient user interface 102 may further be programmed by a user to contact a certain IP address or videoconferencing number corresponding with the medical practitioner user interface 4 (FIG. 1-2), so that the patient user interface 102 automatically connects to the medical practitioner user interface 4 when placed into operation by a patient. In some embodiments, multiple numbers may be programmed into the patient user interface 102 so that the patient user interface 102 may contact multiple medical practitioners in the event that one or more medical practitioners are unable to be contacted immediately. In yet other embodiments, the patient user interface 102 may be programmed with a dispatch number that reroutes the patient user interface 102 to any of a number of medical practitioners.

Figure 15:
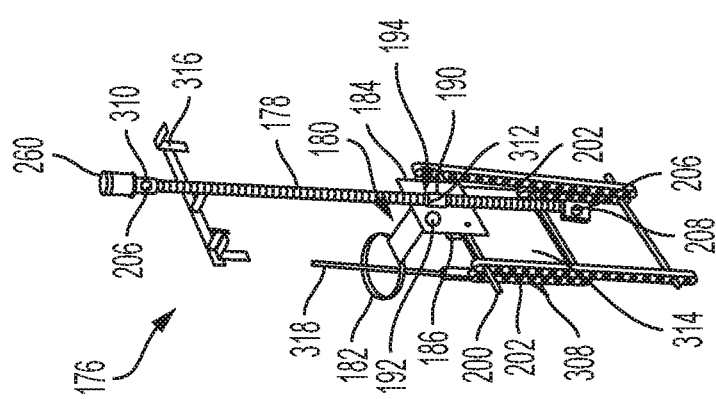
FIG. 15 is a rear perspective view of an instrument assembly of the instrument docking station of FIG. 14.
Figure 24:
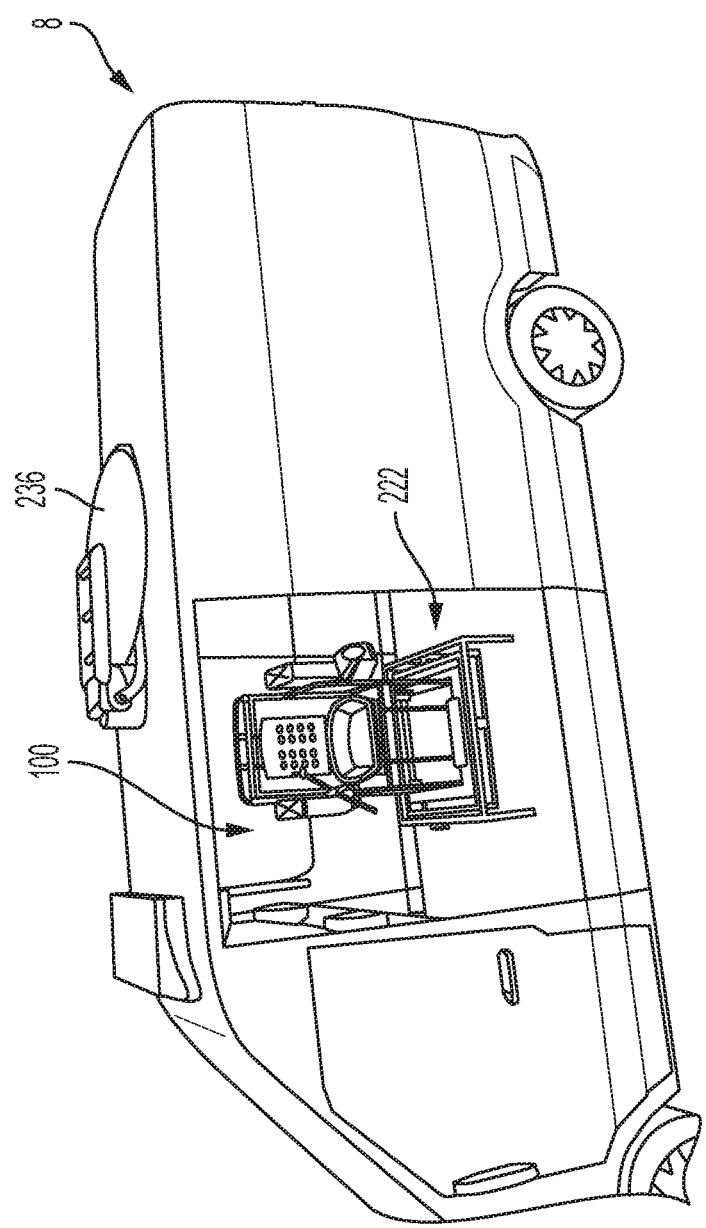
FIG. 24 is a perspective view of a mobile embodiment of the medical chair of FIG. 1, wherein the mobile embodiment is in an undeployed configuration.
Figure 25:
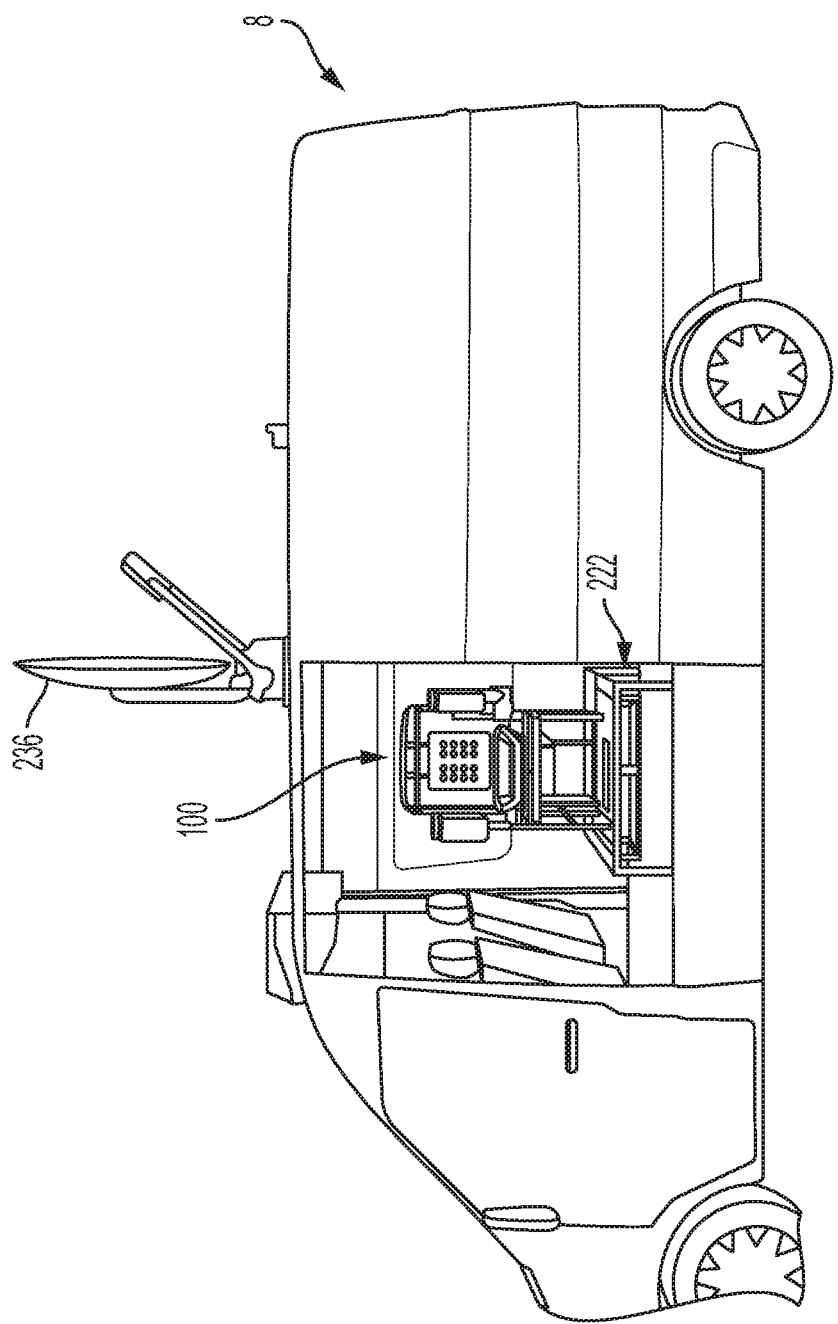
FIG. 25 is a plan view of the mobile embodiment of FIG. 24, wherein the mobile embodiment is in a deployed configuration.

Now referring to FIGS. 24-25, the medical chair 100 may also be mounted within a vehicle 8 to provide for a mobile medical clinic. In such an environment, the medical chair 100 may be operatively coupled to the vehicle power supply, such as a vehicle 12v DC power supply, or rely on the internal power supply for operation. A satellite 236 or other remote connection module may be mounted to the vehicle 8 to allow for remote connection of the medical chair 100 to the medical practitioner user interface 4 (FIGS. 1-2). When the vehicle 8 is in motion or the medical chair 100 is otherwise not available for use, the satellite 236 may be placed in an undeployed configuration as shown in FIG. 24 to protect the satellite 236 from environmental or accidental damage. When the medical chair 100 is in use or ready for use, the satellite 236 may be placed in a deployed configuration as shown in FIG. 15 to facilitate a strong satellite connection. Generally, the setup of the medical chair 100 in a mobile setting is the same as the setup of the medical chair 100 in a stationary setting.

As shown in FIGS. 24-28, the medical chair 100 may be mounted on an auto-level device 222 in either a vehicle 8 or other location to ensure the medical chair 100 is level before use. Specifically referring to FIG. 26, the auto-level device 222 includes an inner frame 224 and an outer frame 226 disposed around the inner frame 224. The inner frame 224 and the outer frame 226 are disposed on an elevation frame 228 that allows for movement of the inner frame 224 and the outer frame 226 without interference from any surface below the auto-level device 222. A positioning module 230, such as a Bluetooth® module, is disposed substantially center of the inner frame 224 so that the module 230 is positioned generally central of the medical chair 100 when mounted on the auto-level device 222.

Figure 26:
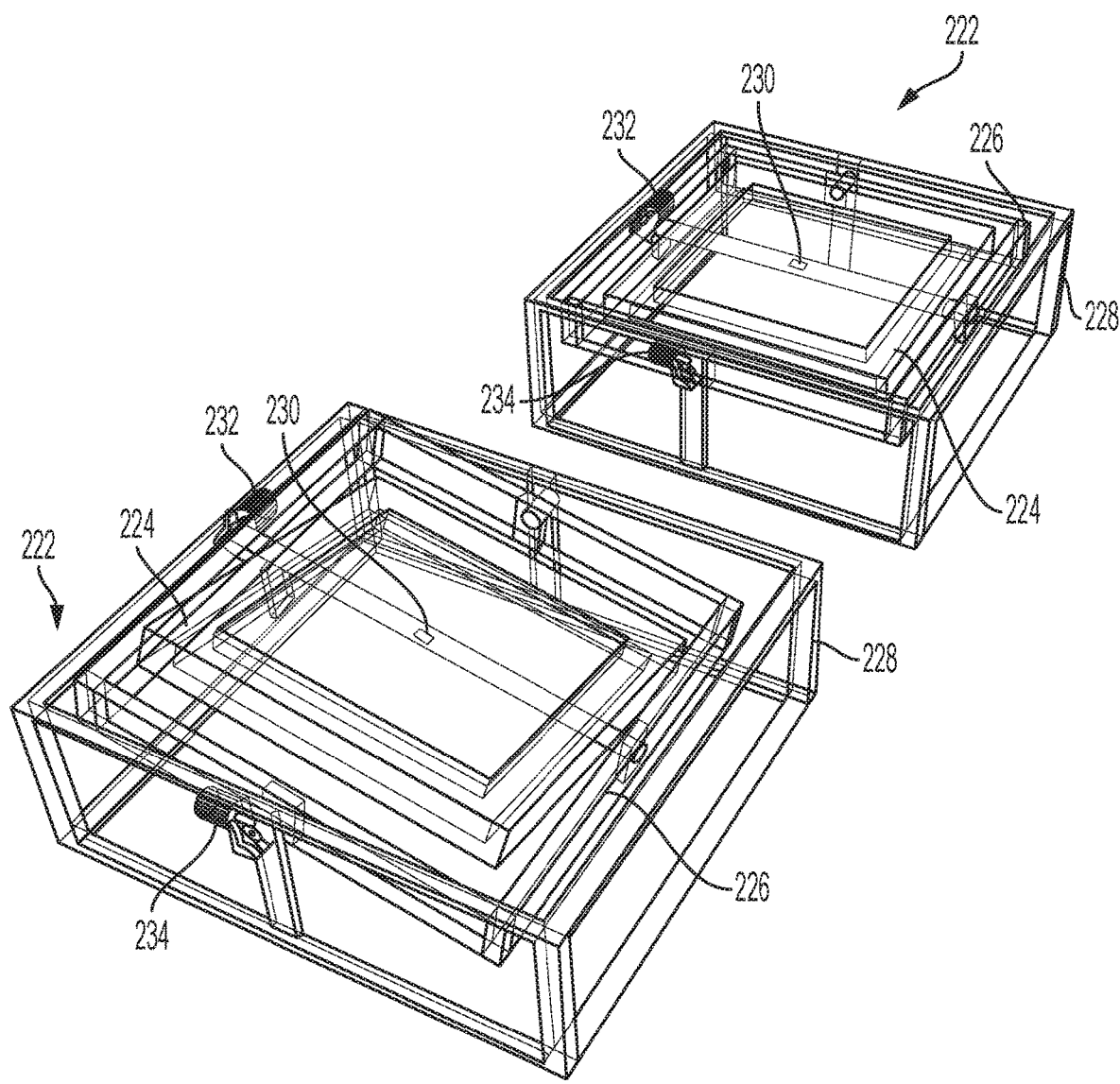
FIG. 26 is a perspective view of an auto-level device for use with the medical chair of FIG. 1.
Figure 27:
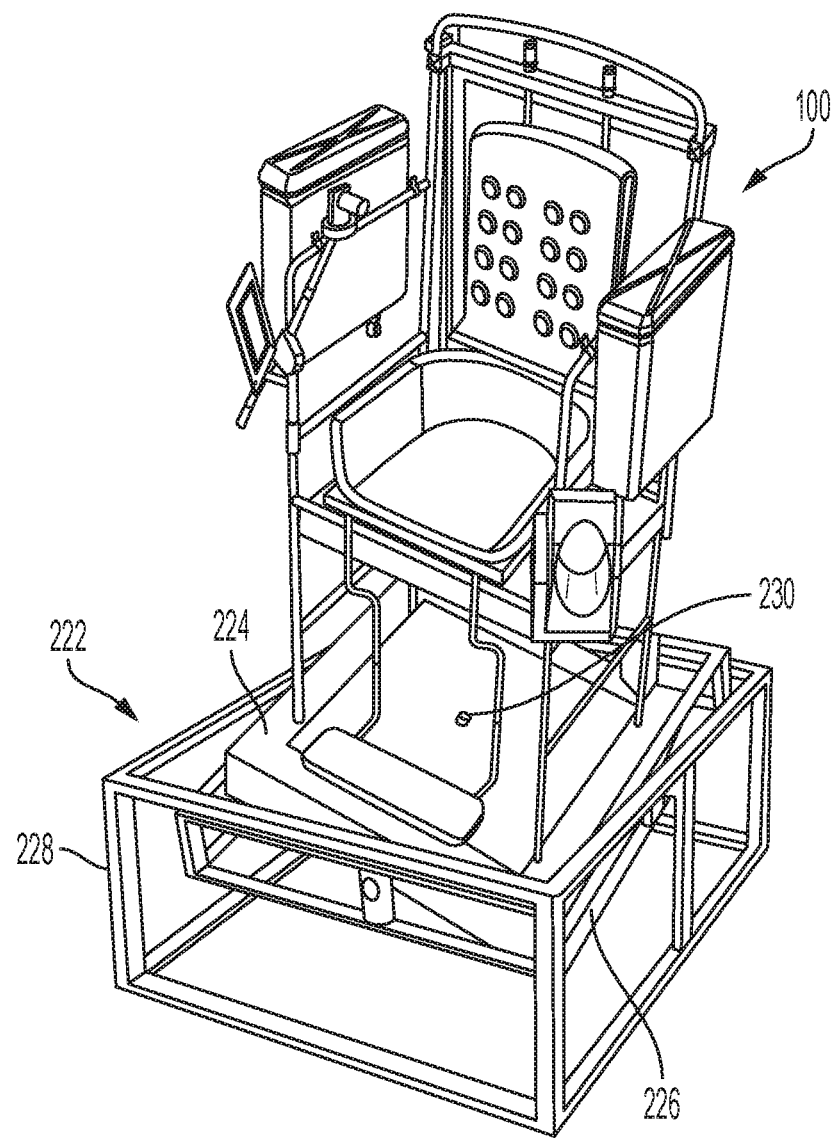
FIG. 27 is a perspective view of the medical chair of FIG. 1 mounted on the auto-level device of FIG. 26.
Figure 28:
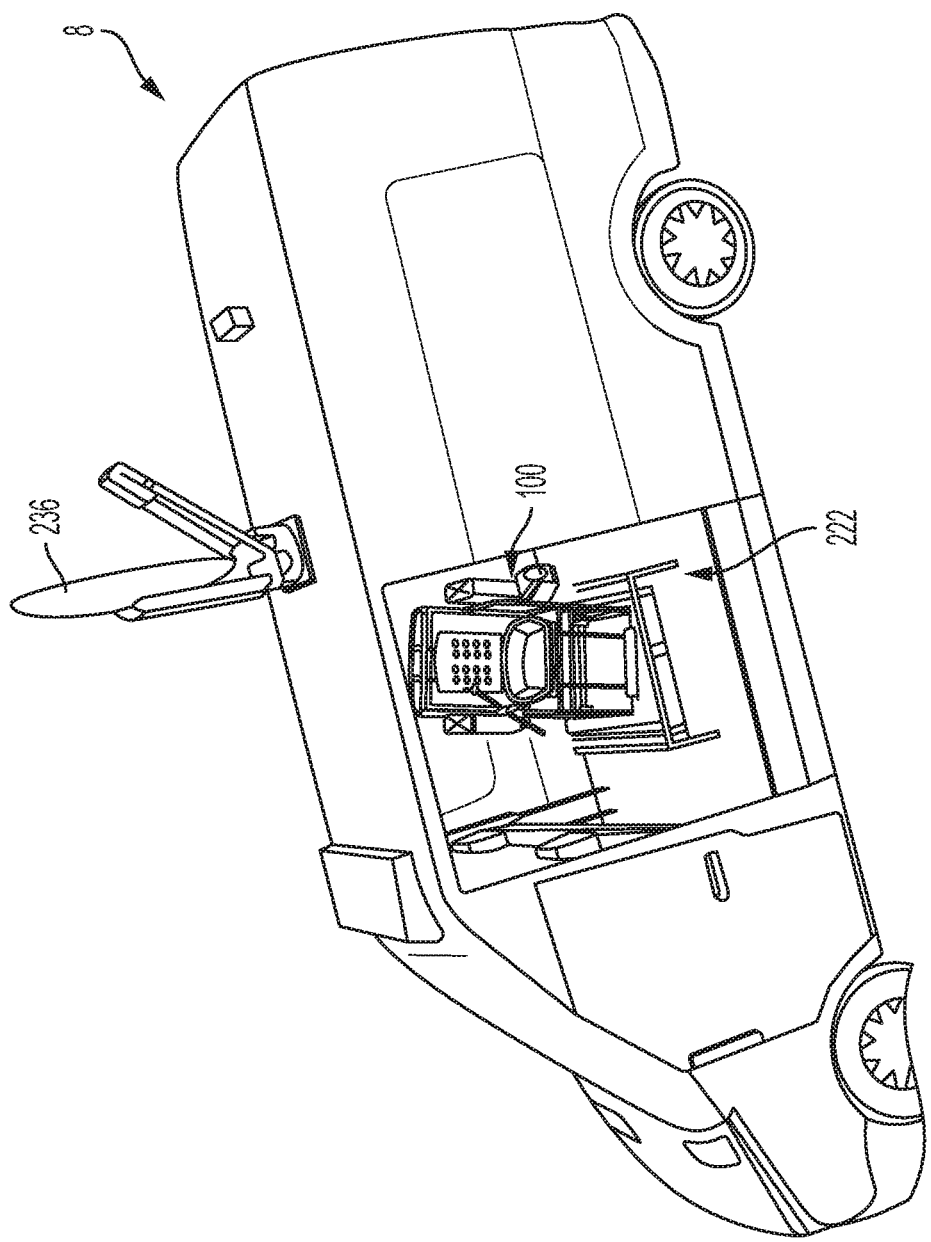
FIG. 28 is a perspective view of a mobile embodiment of the medical chair and auto-level device of FIG. 27.

Referring to FIGS. 26-27, to utilize the auto-level device 222 with a mounted chair 100, the positioning module 230 and the accelerometer 270 (FIG. 23) cooperate to detect deviation from a level position and operate the auto-level device 222 to change position of the inner frame 224 and the outer frame 226 if needed. An inner frame motor 232 is coupled to the inner frame 224 to move, or tilt, the chair 100 in a side-to-side direction. An outer frame motor 234 is coupled to the outer frame 226 to move, or tilt, the chair 100 in a forward-backward direction. The accelerometer 270 (FIG. 23) and the positioning module 230 cooperate to generate data related to the position of the medical chair 100, i.e., whether the medical chair 100 is level, and provide the data to the central computer 238 (FIG. 23). If the medical chair 100 position is in need of adjusting, the central computer 238 (FIG. 23) communicates with the positioning module 230 to operate the inner frame motor 232, the outer frame motor 234, or both the inner frame motor 232 and the outer frame motor 234 to compensate for any tilting or unevenness of the environment. Referring briefly to FIG. 23, communication between the central computer 238, the accelerometer 270, and the positioning module 230 may occur via the Bluetooth® module 272 positioned within the seat drawer 142 as described above.

Now referring again briefly to FIGS. 1-2, during operation, the patient interacts with the patient user interface 102 to place the medical chair 100 into an operation mode and establish a connection with a medical practitioner user interface 4, either via an Internet connection or satellite connection dependent on the medical chair's environment. Once the connection is established, the patient 2 and the medical practitioner 6 ideally have two-way audio and video connectivity to allow for ease of communication between the patient 2 and the medical practitioner 6. The central computer 238 (FIG. 23) and the accelerometer 270 (FIG. 23) monitor whether the medical chair 100 is level as described above.

Referring now to FIGS. 1-23, the medical practitioner 6 may then ask the patient 2 to stand under the ultrasonic sensor 154 of the height sensor 150, which communicates the measured height of the patient 2 to the central computer 238 where it is stored and communicated to the medical practitioner 6. The patient 2 may then sit on the seat scale 110 and place his or her feet on the footrest 112. The magnetic sensors 134 mounted within or to the seat 108 determine whether the patient 2 is sitting upright in the seat to provide an even load to the weight sensors 116 and provide an accurate reading, while the magnetic sensors 140 mounted to the front legs 124a of the medical chair beneath the footrest 112 determine whether the patient 2 has both feet placed on the footrest 112. Such data is communicated to the medical practitioner user interface 4 so that the medical practitioner 6 can request movement of the patient 2 if needed. Once the patient 2 is properly positioned, the medical practitioner 6 may activate the weight sensors 116 via the medical practitioner user interface 4 and the central computer 238 to measure the patient's weight and provide the data to the central computer 238, where it is stored. The central computer 238 may use the recorded height and weight of the patient to calculate the patient's body mass index and communicate such information to the medical practitioner user interface 4.

The patient 2 may position his or her arm within the blood pressure cuff 220, which may be activated by the medical practitioner 6 via the medical practitioner user interface 4 and the central computer 238 to measure the patient's blood pressure. The blood pressure cuff 220 provides the measured data to the central computer 238, which transmits the information to the medical practitioner user interface 4.

The patient 2 may lean back against the back support 156 and stethoscope array 120. The medical practitioner 6 may raise or lower the back support 156 as needed via the central computer 238 and the medical practitioner user interface 4 to align the stethoscope array 120 with the patient's lungs. Specifically, the medical practitioner 6 may utilize the medical practitioner user interface 4 and the central computer 238 to selectively listen to each of the electric sensors 168 comprising the stethoscope array 120 until the patient's lungs can be heard sufficiently or raise or lower the back support 156 accordingly until the patient's lungs can be heard. Such data may be stored in the central computer 238 for transmission to the medical practitioner user interface 4.

The medical practitioner 6 may utilize the medical practitioner user interface 4 and the central computer 238 to activate any one of the instrument assemblies 176 within either of the docking stations 172 to provide the patient 2 with the corresponding instrument for use as described above. The medical practitioner 6 may further instruct the patient 2 to manipulate the spirometer boom 216 and blow into the spirometer 214, which may provide data to the central computer 238 for storage and transmission to the medical practitioner user interface 4.

Referring to FIGS. 1 and 23, the central computer 238 is also configured to maintain a routine to monitor TCP/IP protocol by transmitting "Keep Alive" packets between the medical chair 100 and the medical practitioner user interface 4 every 45-60 seconds and monitoring such transmission. If the central computer 238 fails to detect a continuous series of three Keep Alive packets transmitted between the medical chair 100 and the medical practitioner user interface 4, the connection between the medical chair 100 and the medical practitioner user interface 4 is presumed to have failed. Once failure is presumed, the central computer 238 directs the patient user interface 102 to issue an audio signal, a visible signal, or both, to indicate the loss of the connection. The central computer 238 proceeds to shut down the medical chair 100 by retracting all instruments to their corresponding docking stations 172 and retreating to a standby mode until further use.

Now referring to FIGS. 29-31, a medical chair 1000a illustrating a first configuration of a medical chair 1000 and a medical chair 1000b illustrating a second configuration of a medical chair 1000 are disclosed. The medical chairs 1000 include components similar to the components described above in relation to medical chair 100. Components generally similar between medical chair 100 will be similarly numbered below in relation to medical chairs 1000, adding "1000" to the reference number, with any differences highlighted below. The positions of any of the various components of the medical chairs 1000 may be imputed to the other of the medical chairs 1000 without necessarily changing the positions of every other component as illustrated. In other words, a variety of configurations of the medical chair 1000 exists according to the positioning and function of the various components of the medical chairs 1000 as discussed herein, and the configurations of the medical chairs 1000 are not limited to the exact configurations as shown.

The medical chairs 1000 include a floor base 1500 to support a tube frame 1104 providing handles 1170 for selective or semi-permanent mounting of the medical chair components as discussed herein and providing of support to a user entering or exiting the medical chair 1000. The floor base 1500 preferably comprises a stiff engineered structure to provide rigidity and stability to the floor base 1500 so that the floor base 1500 is capable of providing general support to the medical chair 1000, a user thereof, and/or various components of the medical chair 1000. While the floor base 1500 is illustratively a rectangular shape, the floor base 1500 may comprise a circular shape, an oval shape, another quadrilateral shape, a pentagonal shape, a hexagonal shape, an octagonal shape, or a variety of other shapes that allow for the support of the medical chair 1000.

A plurality of load cells, or weight sensors 1116, are coupled to a bottom surface 1502 of the floor base 1500 so that the floor base 1500 may serve as a scale. The weight sensors 1116 are calibrated during manufacture and installation of the chair 1000 to ensure accurate weight measurement, the weight of the components of the medical chair 1000 tared, or zeroed, during installation and at regular intervals thereafter so that during use only the weight of the patient is measured without the unnecessary weighing of the medical chair 1000 and its components. The weight sensors 1116 cooperate with the floor base 1500 to measure the weight of the patient and communicate the data to a central computer 1238 (FIG. 35) for storage and transmission when activated by the medical practitioner interface 4 (FIGS. 1-2) or the patient user interface 1002.

Illustratively, a weight sensor 1116 is coupled to the bottom surface 1502 of the floor base 1500 at each of the four corners of the floor base 1500 so that the weight of the medical chair 1000 is evenly distributed among the weight sensors 1116. In other embodiments, a fewer or greater number of weight sensors may be utilized and positioned at other points of the floor base 1500, as long as the weight sensors 1116 are distributed such that the weight of the medical chair 1000 and any patient thereon is equally distributed among the weight sensors 1116 to provide for an accurate weight measurement.

Referring to FIGS. 30A-30B, a pair of wheels 1146 are rotatably coupled to the floor base 1500 by a wheel carrier 1504 and provide a deployed configuration to facilitate transportation of the medical chair 1000 as shown in FIG. 30B and an undeployed configuration to prevent unwanted movement of the medical chair 1000 as shown by 30A and allow the weight sensors 1116 to fully contact the surface beneath the medical chair 1000. When the wheels 1146 are in the deployed configuration 1, a user may tilt the chair backwards using tube frame 1104 to support the medical chair 1000b by the wheels 1146 and roll the chair to a new destination. When the wheels 1146 are in the undeployed configuration, the wheels are rotated upwards in a direction away from the floor base 1500 to prevent contact between the wheels 1146 and any surface beneath the medical chair 1000a, avoiding unwanted movement of the medical chair 1000a and allow the weight sensors 1116 to fully contact the surface beneath the medical chair 1000. The undeployed configuration of the wheels 1146 further stows the wheels 1146 to avoid any tripping or falling hazards.

In other embodiments, the wheels 1146 may removably couple to each corner of the medical chair 1000 so that, when in a transportation configuration, the medical chair is spaced apart from any surface beneath the medical chair 1000 to facilitate transportation of the medical chair 1000. In yet further embodiments, the wheels 1146 may removable couple to at least two corners of the medical chair 1000 to facilitate transportation of the medical chair 1000. In any embodiment including removable wheels 1146, the wheels 1146 may be uncoupled from the medical chair 1000 when the medical chair 1000 is deployed for use and stored in a receptacle stored between a seat 1108 of the medical chair 1000 and the floor base 1500 or stored elsewhere either near, attached to, or remote from the medical chair 1000.

Referring again to FIGS. 29-31, the medical chair 1000 includes the seat 1108 supported by legs 1124 to allow the patient a place to sit for comfortability during the course of the examination. A back support 1156 is coupled to the seat 1108 by a plurality of back support arms 1506. Illustratively, the medical chair 1000 includes a pair of back support arms 1506. In other embodiments, the medical chair 1000 may include only one back support arm 1506 or a greater number of back support arms 1506. The back support 1156 may be raised or lowered relative to the seat 1108 according to a method similar to that used in reference to the back support 156 of the medical chair 100 above, with the components required for such a method incorporated with a frame of the back support 1156. The back support 1156 includes a stethoscope array 1120 comprising a plurality of electric sensors 1168 generally arranged on the back support 1156 in a geometric arrangement to facilitate the contact of the electric sensors 1168 with the patient's back.

Figure 33:
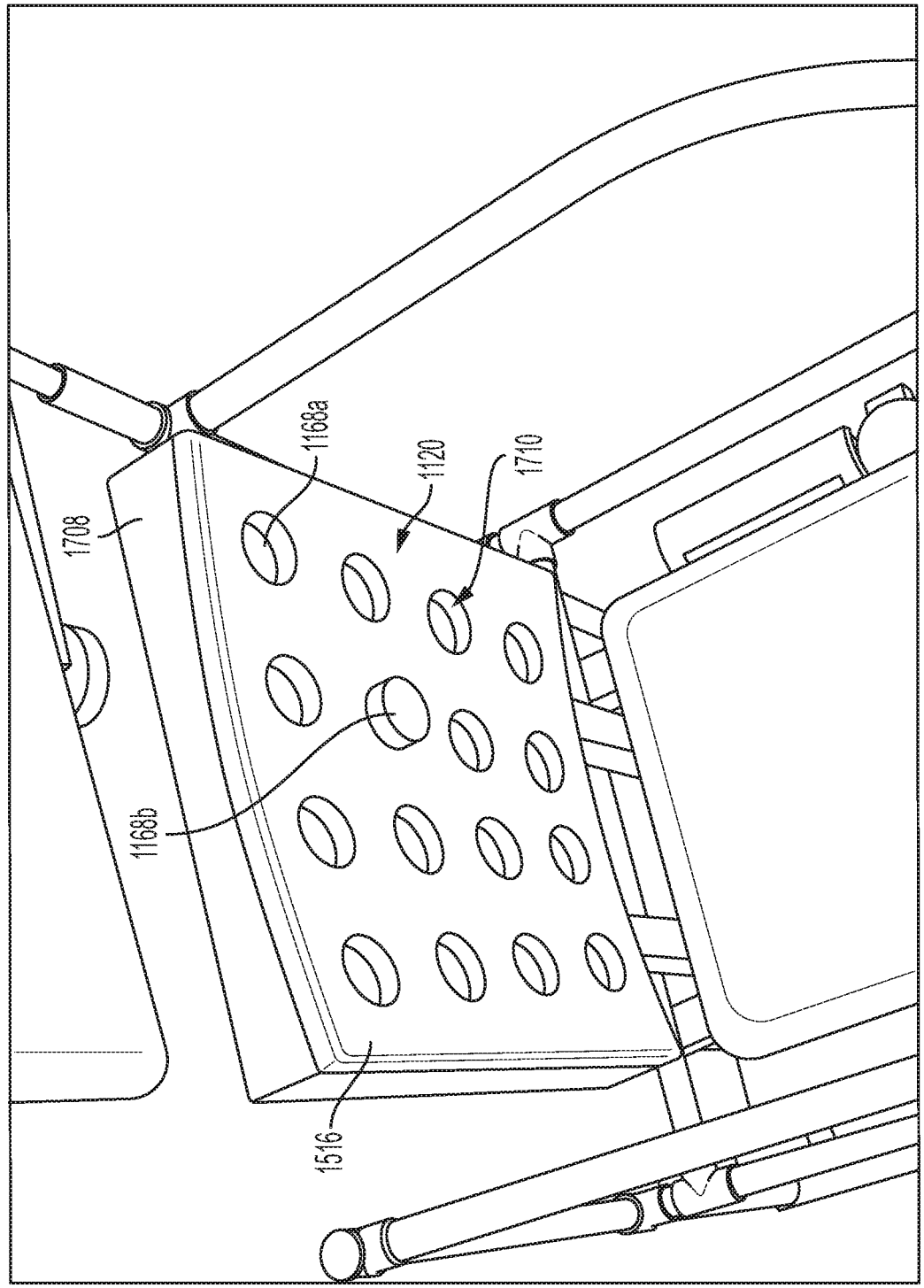
FIG. 33 is a close-up perspective view of a seat back of the medical chair of FIG. 29A, including an exemplary illustration of a stethoscope array having a plurality of undeployed electric sensors and a deployed electric sensor.

The back support 1156 may comprise a comfort layer 1516 of foam or rubber disposed on a rigid layer 1708 of a rigid polymer or metal, most clearly seen in FIG. 33, to provide extra comfort to the patient while maintaining a supportive back support structure. A membrane sleeve 1518 may removably cover the back support 1156 to protect the electric sensors 1168. Specifically, the membrane sleeve 1518 may protect the electric sensors from sweat, debris, or other harmful foreign substances and objects. The membrane sleeve 1518 is at least partially air or sound-wave permeable to allow the passage of air pressure or sound-waves to pass through the membrane sleeve 1518 to the electric sensors 1168.

As shown in FIGS. 30-31, the back support arms 1506 are rotatably coupled to a set of seat support arms 1508 to allow the recline of the back support 1156. The reclining of the back support 1156 provides comfortable support to the patient during use of the medical chair 1000 and may also facilitate alignment of the patient's lungs with the electric sensors 1168 in cooperation with movement of the back support upward or downward relative to the seat 1108 as discussed above. Reclining of the back support 1156 may also be beneficial in situations where the medical practitioner 6 (FIG. 1) wants to monitor a patient's status over an extended period of time so that the patient can be afforded further comfort.

As shown in FIG. 31, a back support crossbar 1510 may span a distance defined by the back support arms 1506 to provide further stability to the back support arms 1506. Similarly, a seat support crossbar 1512 may span a distance defined by the seat support arms 1508. A reclining support 1514 may further span the distance defined by the back support crossbar 1510 and the seat support crossbar 1512. Illustratively, the reclining support 1514 comprises a motorized linear actuator 1515 communicatively coupled to the central computer 1238 (FIG. 35) and configured to shorten or lengthen. When the linear actuator 1515 shortens, the linear actuator 1515 pulls the back support crossbar 1510 toward the seat support crossbar, causing the back support arms 1506 to pivot relative to the seat support arms 1508, resulting in the reclining of the back support 1156 to provide an ergonomically friendly reclining position. When the linear actuator 1515 lengthens, force is provided to the back support crossbar 1510 to push the back support crossbar 1510 away from the seat support crossbar, causing the back support arms 1506 to pivot relative to the seat support arms 1508, resulting in the return of the back support 1156 to an erect position. In other embodiments, when pressure is applied to the back support 1156 or the back support 1156 is motorized to recline, the forward movement of the back support crossbar 1510 is translated to the seat support crossbar 1512 through the reclining support 1514, pushing the seat 1108 in a direction away from the back support 1156, resulting in the recline of the back support 1156

Referring again to FIGS. 29-31, a height sensor 1150 is coupled to the tube frame 1104 of the medical chair 1000. The height sensor 1150 has an undeployed configuration as shown by height sensor 1150b and a deployed configuration as shown by height sensor 1150a. The height sensor 1150 includes an ultrasonic sensor 1154 configured to measure a height of a patient when the patient stands underneath the ultrasonic sensor 1154. When deployed, the ultrasonic sensor 1154 is ideally positioned so that an adult can stand underneath the ultrasonic sensor 1154. For example, the ultrasonic sensor 1154 may stand between about 7' and about 8' from a surface beneath the medical chair 1000. As seen most clearly in FIG. 30, a body 1306 of the height sensor 1150 is configured to telescope into the tube frame 1104 in the undeployed configuration and telescope from the tube frame 1104 in the deployed configuration, wherein the body 1306 of the height sensor 1150 is further configured to rotate relative to the tube frame 1104 to facilitate storage of the height sensor 1150 and positioning of the height sensor 1150 when in use.

The ultrasonic signal is transmitted from the ultrasonic sensor 1154 to the top of the patient's head, wherein the ultrasonic signal reflects from the patient's head to be received by the ultrasonic sensor 1154. A circuit 1155 (FIG. 35) of the height sensor assembly 1150 measures the delay between the transmittal of the ultrasonic signal and the reception of the reflected ultrasonic signal to calculate the height of the patient. The circuit is communicatively coupled to the central computer 1238 (FIG. 35) so that the measured height of the patient can be communicated by the circuit to the central computer 1238 (FIG. 35) for further transmittal and storage.

A boom 1520 includes a first boom portion 1522 rotatably coupled to a handle 1170 of the medical chair 1000 to allow rotation of first boom portion 1522 about an axis substantially similar to a central longitudinal axis of the handle 1170. The first boom portion 1522 is coupled to a second boom portion 1524 via a rotational joint 1526 so that the first boom portion 1522 and the second boom portion 1524 are rotatable relative to each other. The patient user interface 1102 is mounted to the second boom portion 1524 so that a patient may manipulate the boom 1502 to position the patient user interface 1102 as desired. A motor 1528 may be mounted to the handle 1170 and in operative communication with the boom 1520 so that movement of the boom is motorized. For example, at least one proximity sensor may be mounted to the boom 1520 so that the boom automatically changes position when a patient approaches to enter or exit the medical chair 1000 and again changes position to provide access to the patient user interface 1102 once the patient is seated. In other embodiments, the medical practitioner 6 (FIG. 1) may operate the boom 1520 via the medical practitioner user interface 4 (FIGS. 1-2). In such an embodiment, the motor 1528 is in operative communication with the central computer 1238 (FIG. 35) for operation and control of the boom 1520 and transmission of data.

Still referring to FIGS. 29-31, an instrument docking station 1530 is disposed on each side of the medical chair 1000. As shown in relation to the medical chair 1000b, in an undeployed configuration, the instrument docking station 1530 is uncoupled from the tube frame 1104 and positioned on the floor base 1500 for storage to preserve space by reducing an overall width of the medical chair 1000. This reduction in width facilitates easier transportation of the medical chair 1000 through narrow doorways while minimizing the chance of damage to the instrument docking station 1530 during transportation or repositioning. In a deployed configuration, shown in relation to the medical chair 1000b, the instrument docking station is coupled to the tube frame 1104 via brackets 1532. In other embodiments, other removable coupling mechanisms may be used, including alternate mechanical fasteners. Similarly, a clinical waste receptacle 1534 may be removably coupled to the tube frame 1104.

Figure 32:
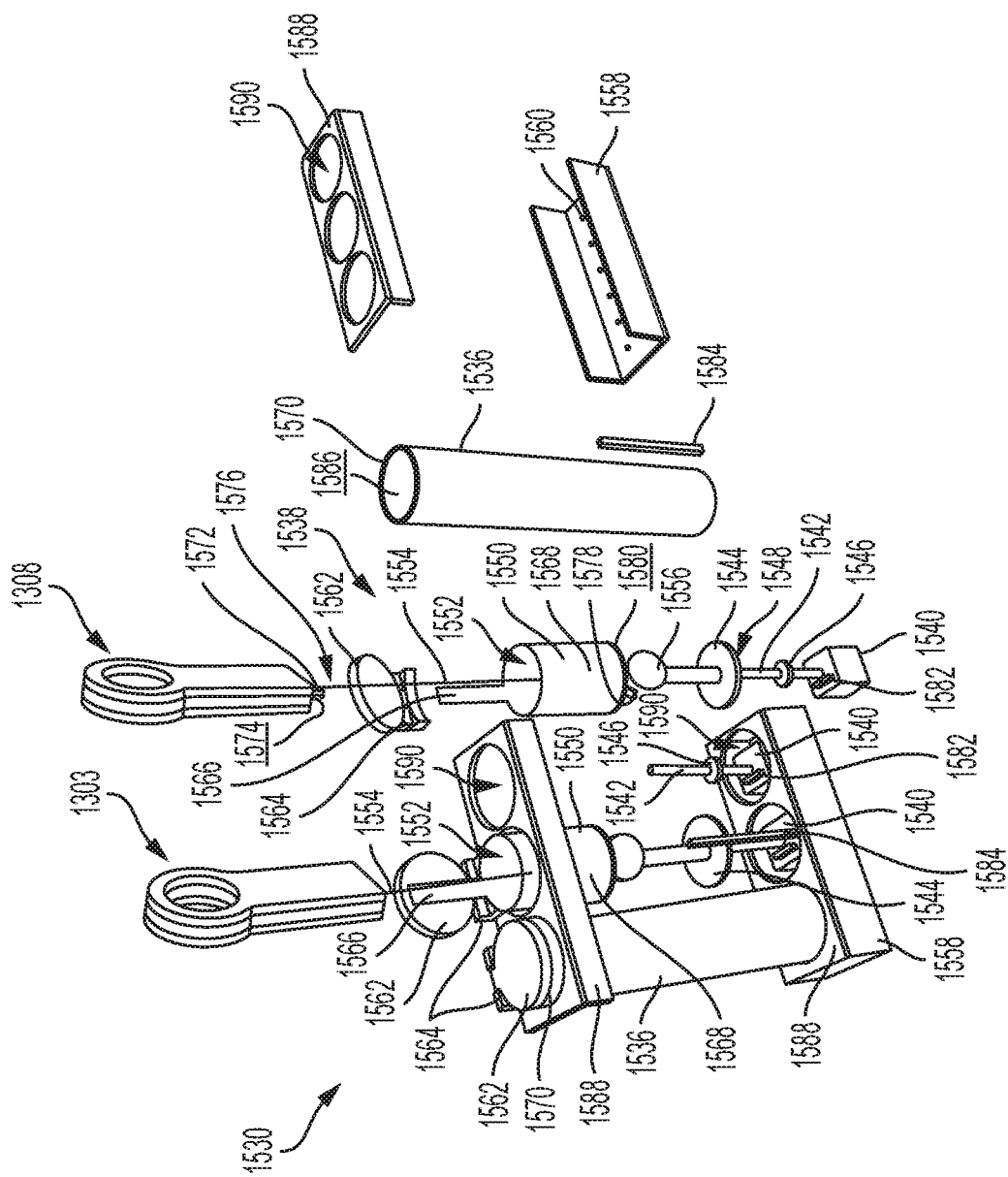
FIG. 32 is a perspective, partially exploded, and exploded view of an instrument docking station and instrument assembly of the medical chair of FIG. 29A.

Now referring to FIG. 32, an illustrative embodiment of the instrument docking station 1530 in an exploded view so that each component of the docking station 1530 is shown. The docking station 1530 includes a plurality of outer tubes 1536, each of the outer tubes 1536 containing an instrument assembly 1538 as described further herein. A lid, or flap 1562 is coupled to each of the outer tubes 1536 by a hinge 1564. The flap 1562 is spring-loaded to bias toward a closed position so that the flap 1562 only opens during operation of the instrument assembly 1538 to prevent unauthorized access to the contained instrument assembly 1538.

The instrument assembly 1538 includes a motor 1540, such as a stepper motor, coupled to a mounting base 1558 of the docking station 1530 via fasteners 1560. The motor 1540 may be coupled to the mounting base 1558 via other coupling methods, including alternative mechanical fasteners or adhesive, for example. The mounting base 1558 may include a base top portion 1588 defining a plurality of openings 1590, each of the openings 1590 sized and shaped to receive one of the outer tubes 1536. The motor 1540 is operably coupled to a leadscrew, or a threaded delivery rod 1542. An anti-rotation disc 1544 defining an anti-rotation slot 1548 is positioned on the delivery rod 1542 above the motor 1540, the anti-rotation disc 1544 coupled to a collar, or nut 1546, which cooperates with the delivery rod 1542 to move the anti-rotation disc 1544 along the delivery rod 1542 during operation of the instrument assembly 1538 as described herein. An instrument support, or a holding tube 1550 configured to store and transport an instrument 1308 is coupled to the anti-rotation disc 1544 to facilitate movement of the holding tube 1550 and corresponding instrument 1550 during operation of the instrument assembly 1538. An anti-rotation bar 1584 is coupled to an inner surface 1586 of the outer tube and received within the anti-rotation slot 1548, preventing unwanted rotation of the anti-rotation disc 1544, the holding tube 1550, and the outer tube 1536 during operation of the instrument assembly 1538 as described herein.

The holding tube 1550 includes a cable aperture (not shown) to allow passage of a security cable 1554 attached to the instrument 1308. The holding tube 1550 defines a holding chamber 1552 for receiving and storing the instrument 1308, which is tethered to the instrument assembly 1538 via the cable 1554 coupled to a retraction spool 1556, which is coupled to the delivery rod 1542 just below the holding tube 1550.

During operation, the motor 1540 rotates the delivery rod 1542 to raise or lower the holding tube 1550 and the instrument 1308 contained therein along the delivery rod 1542. In other words, when the motor 1540 is operational, the delivery rod 1542 rotates either in a first direction to raise the holding tube 1550 or a second direction to lower the holding tube 1550. The holding tube 1550 moves upwards, or towards the flap 1562, to provide access to the instrument 1308, and moves downwards, or away from the flap 1562, to retract the instrument 1308 and prevent access to the instrument 1308. As the holding tube 1550 moves towards the flap 1562, a flap contact 1566 defined by the holding tube 1550 and extending upwards away from a body 1568 of the holding tube 1550 contacts the flap 1562 to push the flap 1562 open, allowing passage of the instrument 1308 beyond an upper edge 1570 of the outer tube 1536 so that the patient can access the instrument 1308 for use. As the patient uses the instrument 1308, the flap contact 1566 maintains the flap 1562 in an open configuration so that the patient may return the instrument 1308 to the holding tube 1550 when use of the instrument 1308 is completed.

A retraction sensor 1578 is disposed on or near a bottom surface 1580 of the holding tube 1550 or on the retraction spool 1556. In some embodiments, the retraction sensor 1578 may be a magnetic sensor, such as a Hall-effect sensor. In such embodiments, an magnet 1572 may be disposed on a bottom surface 1574 of the instrument 1308 or on an upper portion 1576 of the cable 1554. In other embodiments, the retraction sensor 1578 may be an optical proximity sensor having a short range and configured to detect the bottom of the instrument 1308 when the instrument is in close proximity. When the patient has completed use of the instrument 1308 and places the instrument into the holding tube 1550, the retraction sensor 1578 senses the proximity of the magnet 1572 or the instrument 1308 and sends a signal to a motor sensor 1582 of the motor 1540 to lower the holding tube 1550, thereby closing the flap 1562 and preventing further access to the instrument assembly 1538. Ideally, a short delay is provided before the motor 1540 begins to lower the holding tube 1550 to allow the patient to remove his or her hand from the area surrounding the flap 1562. In other embodiments, the retraction sensor 1578 may be configured to sense the retraction or spooling of the cable 1554 around the retraction spool 1556 before sending the appropriate signal to the motor sensor 1578.

The docking station 1530 may include an alignment block 1592 defining alignment openings 1594, each alignment opening 1594 sized and shaped to receive an upper portion 1596 of the outer tube 1536. Each alignment opening 1594 cooperates with the base top portion openings 1590 of the base top 1588 to properly align each outer tube 1536 to facilitate proper operation of the instrument assemblies 1538. As shown in FIGS. 29-31, each docking station 1530 may have four instrument assemblies 1538. In other embodiments, each docking station 1530 may have a greater number of instrument assemblies 1538 or a fewer number of instrument assemblies 1538 as desired. The instruments may include, but are not limited to, a thermometer, an oximeter, a dermascope, an otoscope, a chest piece stethoscope, a blood pressure monitor, a spirometer, or a glucose monitor.

The instruments 1308 may be battery powered or obtain power from a central power supply 1266 (FIG. 35) of the medical chair 1000. In embodiments having rechargeable instruments 1308, a wireless charger, or induction charger, may be implemented within the holding tube 1550 of the instrument assembly 1538 to allow for charging of the instruments 1308 between uses. The instruments 1308 may be enabled with Bluetooth® capabilities or another form of low energy wireless communication so that the instruments 1308 can directly communicate with the central computer 1238 (FIG. 35) of the medical chair 1000 and/or the motor 1540 to operate the corresponding instrument assembly 1538 and its components. In yet other embodiments, the instruments 1308 may be enabled with wireless Internet capabilities, allowing the medical practitioner 6 (FIG. 1) to directly communicate with the instrument 1308 via the medical practitioner user interface 4 (FIGS. 1-2).

Referring now to FIG. 33, an embodiment of a back support 1156 is disclosed. As shown, the electric sensors 1168 of the stethoscope array 1120 are configured to deploy from (1168b) or retract into (1168a) openings 1710 defined by the back support 1156. Such a function may be desired to provide extra protection to the sensors 1168 by retracting the sensors 1168 when not in use, while also providing extra comfort to the patient by preventing unnecessary contact between the patient and the sensors 1168, especially when the back support 1156 is reclined, resulting in extra force being placed on the back support 1156 by the patient's torso.

Figure 34:
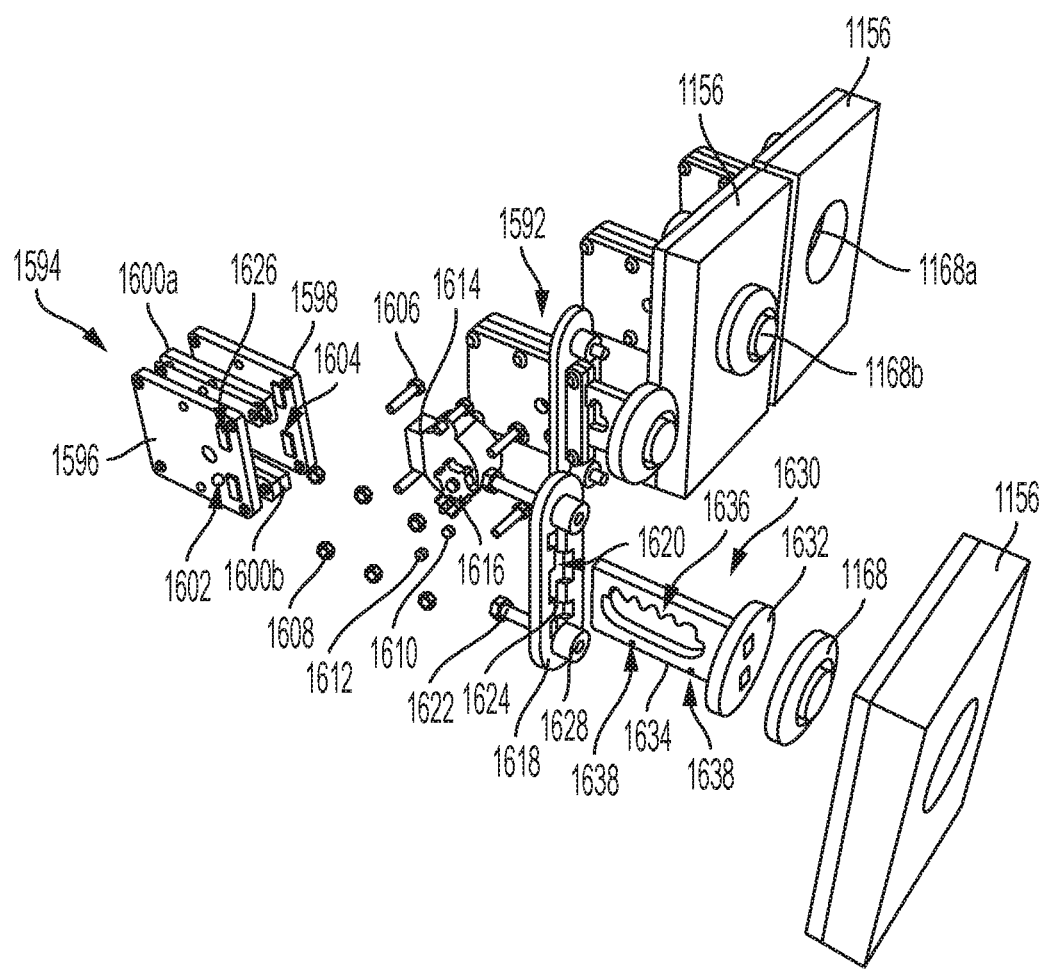
FIG. 34 is a perspective, partially exploded, and exploded view of an actuator system for operation of the electric sensors of FIG. 33.

Now referring to FIG. 34, an actuator system 1592 for deploying and retracting the electric sensors 1168 of the stethoscope array 1120 is provided. The actuator system 1592 includes an actuator frame 1594 comprising a photosensor plate 1596 defining a photosensor aperture 1602, a photoemitter plate 1598 defining a photoemitter aperture 1604, and at least one spacer 1600 disposed between the photosensor plate 1596 and the photoemitter plate 1598. Illustratively, two spacers 1600, upper spacer 1600a and lower spacer 1600b, are utilized to form the actuator frame 1594. In other embodiments, a greater number of spacers 1600 or a fewer number of spacers 1600 may be used for optimal functionality of the actuator system 1592. A signal emitter, or photoemitter 1610 is mounted within the photoemitter aperture 1604 of the photoemitter plate 1598, and a signal receiver, or photosensor 1612 is mounted within the photosensor aperture 1602 of the photosensor plate 1596.

Figure 35:
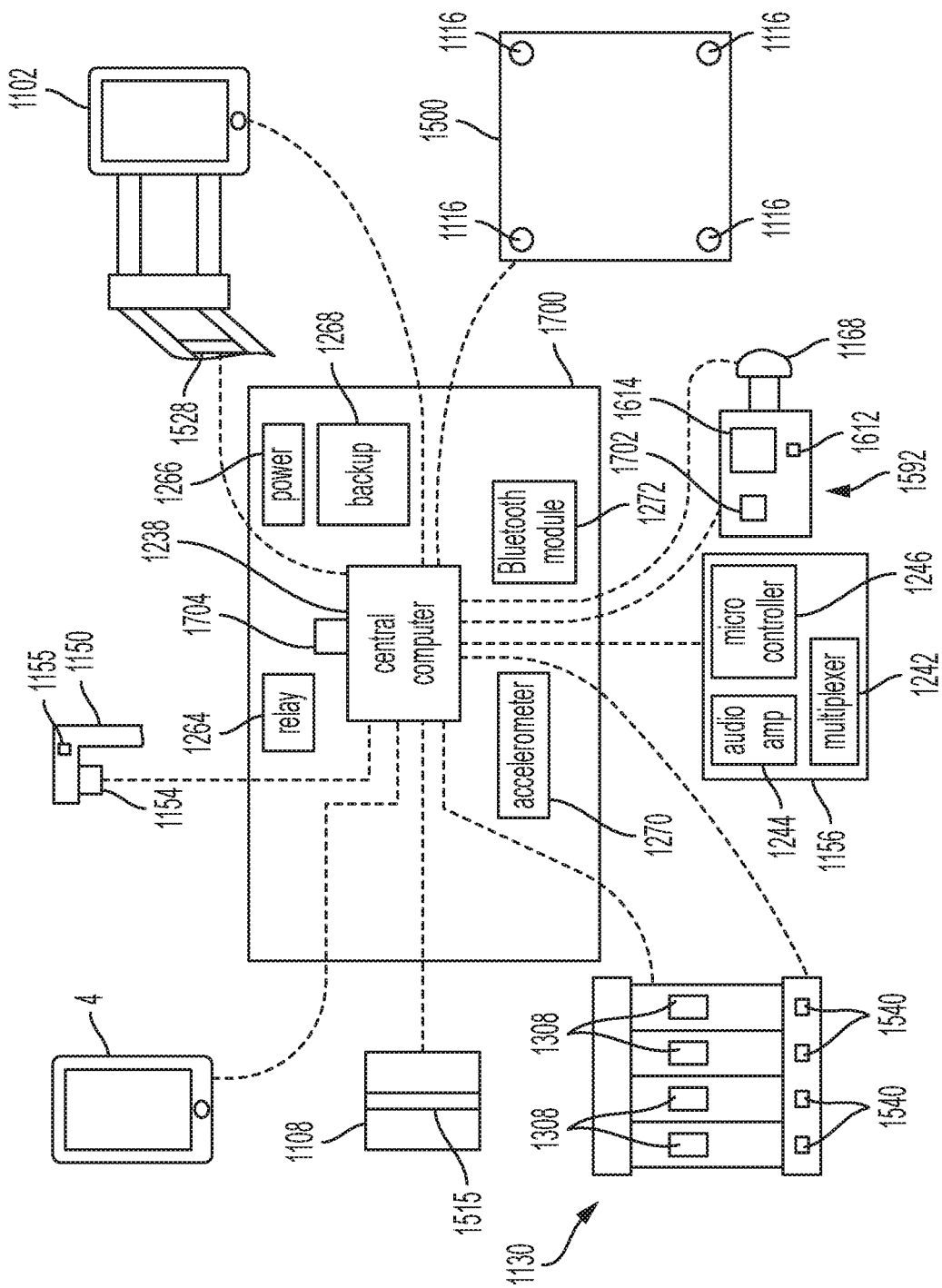
FIG. 35 is a schematic view of the electronic components of the medical chair of FIG. 29A.

The photosensor plate 1596, the photoemitter plate 1598, and the at least one spacer 1600 are fastened together using a plurality of fasteners, illustratively bolts 1606 and nuts 1608. In other embodiments, other fasteners may be utilized. The bolts 1606 are also utilized to mount a motor 1614 to the actuator frame 1594, the motor 1614 coupled to a gear 1616 and operatively coupled to a microcontroller 1702 (FIG. 35). A mounting plate 1618 receives the actuator frame 1594 within an opening 1620 of the mounting plate 1618 sized and shaped to receive the actuator frame 1594. The opening 1620 of the mounting plate 1618 illustratively includes keys 1624 configured to be received within key openings 1626 of the actuator frame 1594 to secure the mounting plate 1618 to the actuator frame 1594. Fasteners 1622 are disposed through the mounting plate 1618 to secure the mounting plate 1618, the actuator frame 1594, and the motor 1614 to the back support 1156. Spacing bolts 1628 may be utilized in a manner that positions the spacing bolts 1628 between the mounting plate 1618 and the back support 1156 to ensure proper positioning of the actuator system 1592 relative to the back support 1156.

The electric sensor 1168 is coupled to a mounting head 1632 of an actuator key 1630. The actuator key 1630 includes a key portion 1634 extending from the mounting head 1632. The key portion 1634 defines an internal rack 1636 configured to cooperate with the gear 1616 and two photosensing slots 1638. The key portion 1634 is received by the actuator frame 1592 to mate the gear 1616 with the internal rack 1636 and to selectively align the photosensing slots 1638 with the photosensor aperture 1602 of the photosensor plate 1596 and the photoemitter aperture 1604 of the photoemitter plate 1598.

Referring additionally to FIG. 35, the photosensor 1612 and the photoemitter 1610 are placed in selective communication with each other through the photosensor aperture 1602, the photoemitter aperture 1604, and the photosensing slots 1638. The photosensor 1612 is communicatively coupled to a microcontroller 1702 in communication with the central computer 1238 so that the microcontroller 1702 receives a photosignal from the photosensor 1612 when the photosensor 1612 and the photoemitter 1610 are placed in communication, allowing the position of the actuator key 1630 and the electric sensor 1168 to be identified by the microcontroller 1702 and transmitted to the central computer 1238. To deploy the electric sensors 1168, the central computer 1238 signals the microcontroller 1702 to place the motor 1614 in operation according to instruction received from the medical practitioner user interface 4 (FIGS. 1-2) or the patient user interface 1102 (FIG. 29). The motor 1614 rotates the gear 1616, which accordingly interacts with the internal rack 1636 of the actuator key 1630 to deploy the electric sensor as shown by 1168a. Similarly, to retract the electric sensors 1168, the central computer 1238 signals the microcontroller 1702 to place the motor 1614 in operation according to instruction received from the medical practitioner user interface 4 (FIGS. 1-2) or the patient user interface 1102 (FIG. 29). The motor 1614 rotates the gear 1616, which accordingly interacts with the internal rack 1636 of the actuator key 1630 to retract the electric sensor as shown by 1168b.

The photosensor 1612 and the photoemitter 1610 are in communication when the electric sensors 1168 are fully deployed and when the electric sensors 1168 are fully retracted. In other words, when the electric sensors 1168 are in the retracted position 1168b, the microcontroller 1702 may operate the motor 1614 to deploy the electric sensors 1168. As the actuator key 1630 moves with operation of the motor 1614, the photosensor 1612 and the photoemitter 1610 lose communication. When the photosensor 1612 and the photoemitter 1610 regain communication, the electric sensors 1168 are in the deployed position 1168a, and the microcontroller 1702 receives a signal from the photosensor 1612, stopping operation of the motor 1614.

Similarly, when the electric sensors 1168 are in the deployed position 1168a, the microcontroller 1702 may operate the motor 1614 to retract the electric sensors 1168. As the actuator key 1630 moves with operation of the motor 1614, the photosensor 1612 and the photoemitter 1610 lose communication. When the photosensor 1612 and the photoemitter 1610 regain communication, the electric sensors 1168 are in the retracted position 1168b, and the microcontroller 1702 receives a signal from the photosensor 1612, stopping operation of the motor 1614.

Such operation allows for autocorrection of electric sensor positioning. For example, if the electric sensors 1168 are in the deployed position 1168a and the electric sensors 1168 are subjected to a force that places the sensors 1168 in a partially retracted position, the photoemitter 1610 and the photosensor 1612 unexpectedly lose communication. The microcontroller 1702 receives a signal from the photosensor 1612, and the microcontroller 1702 automatically places the motor 1614 in operation to remedy the position of the sensors 1168. To mitigate against constant slippage or movement of the electric sensors 1168, a hysteresis may be implemented to allow a reasonable amount of force to be placed on the electric sensors 1168 without resulting in a slippage that requires autocorrection. This is implemented by slightly elongating the photosensing slots 1638 so that the photosensor 1612 and the photoemitter 1610 maintain contact whether the actuator key 1630 is fully extended or slightly depressed.

Additionally, when the electric sensors 1168 are in the deployed position 1168a, the motor 1614 maintains a holding force against the rack 1636 of the actuator key 1630 via the gear 1616 to counteract a reasonable force placed on the electric sensors 1168 from the patient's back due to contact between the patient's back and the electric sensors 1168. The holding force does not result in the creation of any audible noise that would interfere with the operation of the electric sensors 1168. In the event too much force is placed on the electric sensors 1168, the holding force of the motor 1614 may slip, resulting in an autocorrect method described above.

While the actuator system 1592 is in operation, the electric sensors 1168 are electrically disconnected from an audio system 1704 of the central computer 1238 by a plurality of electrical relays 1706. In other words, an electric sensor 1168 is only communicatively coupled to the audio system 1704 of the central computer 1238 when it is stationary. This prevents the operational noise of the actuator system 1592 and other ambient noise from interfering with the sounds of the patient's lungs or heart, which may create only low-level noise.

The components of the actuator system 1592 may be manufactured from a sheet of polymer, such as synthetic resin bonded paper laminate, using a low-cost three axis milling technique which saves costs by foregoing the expensive process of tooling and is suited for specialist and low-volume manufacture. The components of the actuator system 1592 may otherwise be manufactured from pressed metal and/or injection molded polymers for high volume needs.

Referring again to FIGS. 29-31, an electronics enclosure 1700 is positioned beneath the seat 1108 of the medical chair 1000 on the floor base 1500. The electronics enclosure 1700 may be positioned anywhere on the medical chair 1000 that provides convenient access to the contained electronics by the various components of the medical chair 1000. For example, referring specifically to FIG. 35, electronics enclosure 1700 may contain a power supply 1266, a backup power supply 1268, and a relay 1264 to determine when an internal power supply is needed, or if power is being supplied by an outside source to provide power to any control and data processing electronics and medical instruments included with or otherwise coupled to the medical chair 1000. An accelerometer 1270 may also be disposed within the electronics enclosure 1700 to determine whether the chair is positioned on a level surface as discussed further herein. A Bluetooth® module 1272 may be disposed within the electronics enclosure 1700 to transmit or receive Bluetooth® signals as needed. The central computer 1238 is further stored within the electronics enclosure 1700 and includes Wi-Fi or wireless Internet technology and 4G cellular modules for connecting to the Internet. Other embodiments may include technology for wired Internet connections, 5G cellular modules, or other technology providing for remote data transfer as known in the art.

Referring specifically to FIG. 35, the central computer 1238 contained within the electronics enclosure 1700 may transmit and/or receive data from the patient user interface 1102, the medical practitioner user interface 4, the ultrasonic height sensor 1154, the instruments 1308, the motor 1540 of the docking station 1130, the photosensor 1612 of the actuator system 1592, the motor 1614 of the actuator system 1592, the weight sensors 1116 of the floor base 1500, and other components of the medical chair 1000 discussed above or in relation to medical chair 100.

While the invention has been described by reference to various specific embodiments, it should be understood that numerous changes may be made within the spirit and scope of the inventive concepts described. Additionally, features and components described in relation to certain embodiments may also be utilized in other described embodiments. For example, the described deployment and retraction function of the electric sensors of the medical chair 1000 may additionally be utilized in connection with the medical chair 100. Other features and components described herein may also be utilized in any embodiment. Accordingly, it is intended that the invention not be limited to the described embodiments but will have full scope defined by the language of the following claims.

What is claimed is:

1. A medical chair assembly operable by a patient, comprising:
   a seat and a frame comprising a first handle on a first side of the seat;
   a docking station coupled to the first handle, the docking station housing a plurality of instrument assemblies, each instrument assembly comprises an instrument, a holding tube for the instrument, and a motor, wherein operation of the motor moves the instrument assembly from a retracted configuration to a deployed configuration to position the instrument at least partially exposed outside of the docking station and each instrument assembly further includes a retraction sensor to sense when the patient has placed the instrument in the holding tube for the instrument whereby the retraction sensor sends a signal to the motor which retracts the instrument assembly within the docking station.

2. The medical chair assembly of claim 1, wherein each instrument assembly further comprises:
   a threaded rod coupled to the motor and extending a direction away from the motor; and
   an instrument support operably coupled to the threaded rod so that when the threaded rod rotates in a first direction, the instrument support is configured to move along the threaded rod in a first direction and when the threaded rod rotates in a second direction, the instrument support is configured to move along the threaded rod in a second direction.

3. The medical chair assembly of claim 2, wherein movement of the instrument support in the first direction places the instrument assembly in the deployed configuration and movement of the instrument support in the second direction places the instrument assembly in the retracted configuration.

4. The medical chair assembly of claim 1, wherein at least one instrument is tethered to at least one instrument assembly with a retractable cable.

5. The medical chair assembly of claim 4, wherein the instrument is controllable using a user interface remote from the medical chair assembly.

6. The medical chair assembly of claim 1, wherein each instrument assembly further comprises a lid or cover configured to prevent access to the instrument when the instrument assembly is in the retracted configuration.

7. The medical chair assembly of claim 6, wherein direct contact between the instrument assembly and the lid or cover opens the lid or cover as the instrument assembly is moved from the retracted configuration to the deployed configuration.

8. The medical chair assembly of claim 1, wherein at least one of the instrument assemblies is controllable using a user interface remote from the medical chair assembly.

9. The medical chair assembly of claim 1 wherein the frame further comprises a second handle on a second side of the seat, and wherein an additional instrument docking station is coupled to the second handle.

10. The medical chair assembly of claim 1, wherein each of the plurality of instrument assemblies includes a different instrument.

11. The medical chair assembly of claim 1, wherein a majority of the plurality of instrument assemblies includes a different instrument.

12. The medical chair assembly of claim 1, wherein the instrument docking station is removably coupled to the first handle.

* * * * *